(12) United States Patent
Chereze et al.

(10) Patent No.: US 8,148,364 B2
(45) Date of Patent: Apr. 3, 2012

(54) SUBSTITUTED BICYCLIC PYRIMIDONE DERIVATIVES

(75) Inventors: Nathalie Chereze, Paris (FR); Alistair Lochead, Paris (FR); Mourad Saady, Paris (FR); Franck Slowinski, Paris (FR); Philippe Yaiche, Paris (FR)

(73) Assignees: Sanofi-Aventis, Paris (FR); Mitsubishi Tanabe Pharma Corporation, Osaka-Shi, Osaka (JP)

( * ) Notice: Subject to any disclaimer, the term of this patent is extended or adjusted under 35 U.S.C. 154(b) by 687 days.

(21) Appl. No.: 12/122,111

(22) Filed: May 16, 2008

(65) Prior Publication Data
US 2009/0036427 A1 Feb. 5, 2009

Related U.S. Application Data

(63) Continuation of application No. PCT/IB2006/004046, filed on Nov. 21, 2006.

(30) Foreign Application Priority Data

Nov. 21, 2005 (EP) .................................... 05292457

(51) Int. Cl.
- *C07D 239/00* (2006.01)
- *C07D 223/00* (2006.01)
- *A61K 31/55* (2006.01)
- *A61K 31/519* (2006.01)
- *A61P 25/28* (2006.01)

(52) U.S. Cl. ................ 514/214.02; 514/259.5; 544/282; 540/593

(58) Field of Classification Search .................. 544/279, 544/280, 282; 514/259.1, 259.4, 214.02, 514/259.5; 540/593
See application file for complete search history.

(56) References Cited

U.S. PATENT DOCUMENTS

| 4,234,586 A | 11/1980 | Hermecz et al. |
| 2010/0130518 A1* | 5/2010 | Dong et al. ............. 514/264.11 |

FOREIGN PATENT DOCUMENTS

EP 1460076 9/2004

OTHER PUBLICATIONS

Griesser, Ch. 8, The Importance of Solvates (pp. 211-230), in the text, Polymorphism: In the Pharmaceutical Industry, Hilfiker, 2006.*
Britain, pp. 126-127, 2008, <http://www.netlibrary.com/nlreader.dll?bookid=12783&filename=Page_126.html>.*

* cited by examiner

*Primary Examiner* — James O Wilson
*Assistant Examiner* — Cecilia M Jaisle
(74) *Attorney, Agent, or Firm* — Scully, Scott, Murphy & Presser, P.C.

(57) ABSTRACT

A pyrimidone derivative represented by formula (I) or a salt thereof, or a solvate thereof or a hydrate thereof:

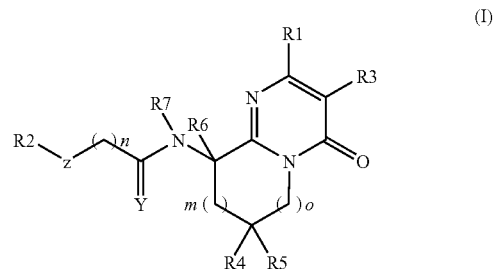

(I)

Wherein Y, Z, R1, R2, R3, R4, R5, R6, R7, n, m, and o are as described herein. The invention relates also to a medicament comprising the said derivative or a salt thereof as an active ingredient which is used for preventive and/or therapeutic treatment of a neurodegenerative disease caused by abnormal activity of GSK3β, such as Alzheimer disease.

10 Claims, No Drawings

SUBSTITUTED BICYCLIC PYRIMIDONE DERIVATIVES

CROSS REFERENCE TO RELATED APPLICATIONS

This application is a continuation of International application No. PCT/IB2006/004,046, filed Nov. 21, 2006, which is incorporated herein by reference in its entirety; which claims the benefit of priority of European Patent Application No. 05292457.8, filed Nov. 21, 2005.

BACKGROUND OF THE INVENTION

1. Field of the Invention

The present invention relates to compounds that are useful as an active ingredient of a medicament for preventive and/or therapeutic treatment of neurodegenerative diseases caused by abnormal activity of GSK3β.

2. Background Art

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases and other pathologies where GSK3β is deregulated (Nature reviews Vol. 3, June 2004, p. 479-487; Trends in Pharmacological Sciences Vol. 25 No. 9, September 2004, p. 471-480; Journal of neurochemistry 2004, 89, 1313-1317; Medicinal Research Reviews, Vol. 22, No. 4, 373-384, 2002).

The neurodegenerative diseases include, in a non-limiting manner, Parkinson's disease, taupathies (e.g. Fronto temporal dementia, corticobasal degeneration, Pick's disease, progressive supranuclear palsy), Wilson's disease, Huntington's disease (The Journal of biological chemistry Vol. 277, No. 37, Issue of September 13, pp. 33791-33798, 2002), Prion disease (Biochem. J. 372, p. 129-136, 2003) and other dementia including vascular dementia; acute stroke and others traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of GSK3β results in neuronal differentiation of embryonic stem cells (ESC) and supports the renewal of human and mouse ESCs and the maintenance of their pluripotency. This suggests that inhibitors of GSK3β could have applications in regenerative medicine (Nature Medicine 10, p. 55-63, 2004).

Inhibitors of GSK3β may also find application in the treatment of other nervous system disorders, such as bipolar disorders (manic-depressive illness). For example lithium has been used for more than 50 years as a mood stabilizer and the primary treatment for bipolar disorder. The therapeutic actions of lithium are observed at doses (1-2 mM) where it is a direct inhibitor of GSK3β. Although the mechanism of action of lithium is unclear, inhibitors of GSK3β could be used to mimic the mood stabilizing effects of lithium. Alterations in Akt-GSK3β signaling have also been implicated in the pathogenesis of schizophrenia.

In addition, inhibition of GSK3β could be useful in treating cancers, such as colorectal, prostate, breast, non-small lung carcinoma, thyroid cancer, T or B-cell leukemia and several virus-induced tumors. For example, the active form of GSK3β has been shown to be elevated in the tumors of colorectal cancer patients and inhibition of GSK3β in colorectal cancer cells activates p53-dependent apoptosis and antagonizes tumor growth. Inhibition of GSK3β also enhances TRAIL-induced apoptosis in prostate cancer cell lines. GSK3β also plays a role in the dynamics of the mitototic spindle and inhibitors of GSK3β prevent chromosome movement and lead to a stabilization of microtubules and a prometaphase-like arrest that is similar to that observed with low doses of Taxol. Other possible applications for GSK3β inhibitors include therapy for non-insulin dependent diabetes (such as diabetes type II), obesity and alopecia.

Recently, both human genetics and animal studies have pointed out the role of Wnt/LPR5 pathway as a major regulator of bone mass accrual. Inhibition of GSK3β leads to the consequent activation of canonical Wnt signaling. Because deficient Wnt signaling has been implicated in disorders of reduced bone mass, GSK3β inhibitors may also be used for treating disorders of reduced bone mass, bone-related pathologies, osteoporosis.

Inhibitors of human GSK3β may also inhibit pfGSK3, an ortholog of this enzyme found in *Plasmodium falciparum*, as a consequence they could be used for the treatment of malaria (Biochimica et Biophysica Acta 1697, 181-196, 2004).

According to recent data, GSK3beta inhibitors might be used in the treatment or prevention Pemphigus vulgaris.

According to recent studies, show that GSK3beta inhibitor treatment improved neutrophil and megakaryocyte recovery. Therefore, GSK3beta inhibitors will be useful for the treatment of neutropenia induced by cancer chemotherapy.

SUMMARY OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides as an object of the invention the pyrimidone derivatives represented by formula (I) or salts thereof, solvates thereof or hydrates thereof:

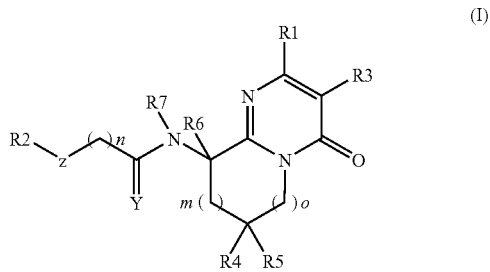

wherein:
Y represents two hydrogen atoms, a sulfur atom, an oxygen atom or a $C_{1-2}$ alkyl group and a hydrogen atom;
Z represents a bond, an oxygen atom, a nitrogen atom substituted by a hydrogen atom or a $C_{1-3}$ alkyl group, a sulfur atom, a methylene group optionally substituted by one or two groups chosen from a $C_{1-6}$ alkyl group, a hydroxyl group, a $C_{1-6}$ alkoxy group, a $C_{1-2}$ perhalogenated alkyl group or an amino group;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a benzene ring or a naphthalene ring; the rings being optionally substituted by 1 to 4 substituents selected from a $C_{1-6}$ alkyl group, $C_{3-7}$ cycloalkyl group, a $C_{3-7}$ cycloalkyl-$C_{1-6}$ alkyl group, a halogen atom, a $C_{1-2}$ perhalogenated alkyl group, a $C_{1-3}$ halogenated alkyl group, a hydroxyl group, a $C_{1-6}$alkoxy group optionally substituted by a $C_{3-5}$ cycloalkyl group, a $C_{1-2}$ perhalogenated alkoxy group, a $C_{1-6}$ alkylsulfonyl group, a nitro, a cyano, an amino, a $C_{1-6}$ monoalkylamino group or a $C_{2-12}$ dialkylamino group, an acetoxy group or an aminosulfonyl group;
R3 represents a hydrogen atom, a $C_{1-6}$ alkyl group or a halogen atom;
R4 represents a hydrogen atom or a $C_{1-6}$ alkyl group;
R5 represents a hydrogen atom, a $C_{1-6}$ alkyl group optionally substituted by 1 to 4 substituents selected from a halogen atom, a phenyl group, a hydroxyl group or a $C_{1-6}$ alkoxy group;
R6 represents a hydrogen atom, a $C_{1-6}$ alkyl group or a halogen atom;
R7 represents a hydrogen atom or a $C_{1-6}$ alkyl group; and
n represents 0 to 3; m represents 0 to 1; o represents 0 to 2.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: Non-insulin dependent diabetes (such as diabetes type II) and obesity; malaria, bipolar disorders (manic depressive illness); schizophrenia; alopecia or cancers such as colorectal, prostate, breast cancer, non-small cell lung carcinoma, thyroid cancer, T or B-cell leukemia, several virus-induced tumors and bone related pathologies. The medicament could also find an application in regenerative medicine.

DETAILED DESCRIPTION OF THE INVENTION

As further embodiments of the present invention, there are provided the aforementioned medicament wherein the diseases are neurodegenerative diseases and are selected from the group consisting of Alzheimer's disease, Parkinson's disease, taupathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis; peripheral neuropathies; retinopathies and glaucoma, and the aforementioned medicament in the form of pharmaceutical composition containing the above substance as an active ingredient together with one or more pharmaceutical additives.

As further embodiments of the present invention, there are provided the aforementioned medicament wherein the bones related pathologies are osteoporosis.

The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group (Me or $CH_3$), ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{1-6}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen atoms have been substituted by a halogen, for example a $CF_3$ or $C_2F_5$;

The $C_{1-3}$ halogenated alkyl group represents an alkyl group wherein at least one hydrogen has not been substituted by a halogen atom;

The $C_{1-6}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group, isopentylamino group and the like;

The $C_{2-12}$ dialkylamino group represents an amino group substituted by two $C_{1-6}$ alkyl groups, for example, dimethylamino group, ethylmethylamino group, diethylamino group, methylpropylamino group and diisopropylamino group and the like;

A leaving group L represents a group which could be easily cleaved and substituted, such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine and arginine. The base-addition salts of acidic compounds are prepared by standard procedures well known in the art.

When a basic group exists, examples include salts with mineral acids such as hydrochloric acid, hydrobromic acid; salts with organic acids such as acetic acid, propionic acid, tartaric acid, fumaric acid, maleic acid, malic acid, oxalic acid, succinic acid, citric acid, benzoic acid and the like.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention.

The pyrimidone derivatives represented by the aforementioned formula (I) may have one or more asymmetric carbon atoms. As for the stereochemistry of such asymmetric carbon atoms, they may independently be in either (R) and (S) configuration, and the derivative may exist as stereoisomers such as optical isomers, or diastereoisomers. Any stereoisomers in pure form, any mixtures of stereoisomers, racemates and the like fall within the scope of the present invention.

Examples of compounds of the present invention are shown in table 1 hereinafter. However, the scope of the present invention is not limited by these compounds.

An object of the present invention includes also compounds represented by formula (I) wherein m, n, o are as defined above and:

(1) R1 represents a 3- or 4-pyridine ring alternatively a 4- or 5-pyrimidine ring; the ring being optionally substituted by a $C_{1-2}$ alkyl group, a $C_{1-2}$ alkoxy group or a halogen atom; and/or (2) R2 represents a benzene ring or a naphthalene ring; the rings being optionally substituted by 1 to 4 substituents selected from a $C_{1-3}$ alkyl group, $C_{3-5}$ cycloalkyl group, a $C_{3-5}$ cycloalkyl-$C_{1-4}$ alkyl group, a halogen atom, a $C_{1-2}$ perhalogenated alkyl group, a hydroxyl group, a $C_{1-3}$ alkoxy group optionally substituted by a $C_{3-5}$ cycloalkyl group, a $C_{1-2}$ perhalogenated alkoxy group, a $C_{1-6}$ alkylsulfonyl group, a nitro, a cyano, an amino, a $C_{1-3}$ monoalkylamino group or a $C_{2-6}$ dialkylamino group; and/or (3) R3 represents a hydrogen atom, a $C_{1-3}$ alkyl group or a halogen atom;

(4) R4 represents a hydrogen atom or a $C_{1-3}$ alkyl group; and/or (5) R5 represents a hydrogen atom, a $C_{1-3}$ alkoxy carbonyl group or a $C_{1-3}$ alkyl group optionally substituted by 1 to 4 substituents selected from a halogen atom, a phenyl group, a hydroxyl group or a $C_{1-3}$ alkoxy group; and/or (6) R6 represents a hydrogen atom, a $C_{1-3}$ alkyl group or a halogen atom; and/or (7) R7 represents a hydrogen atom or a $C_{1-3}$ alkyl group; and/or (8) Y represents two hydrogen atoms, an oxygen atom or a $C_{1-2}$ alkyl group and a hydrogen atom; and/or (9) Z represents a bond, an oxygen atom, a nitrogen atom substituted by a hydrogen atom or a $C_{1-3}$ alkyl group, a methylene group optionally substituted by one or two groups chosen from a $C_{1-3}$ alkyl group, a hydroxyl group, a $C_{1-3}$ alkoxy group, a $C_{1-2}$ perhalogenated alkyl group or an amino group; and/or

(10) n represents 0 to 3;

(11) m represents 0 to 1; o represents 1 to 2; and more particularly wherein R1, R2, R3, R4, R5, R6, R7, m, n, o, Y and Z are as defined here-above.

Another object of the present invention includes compounds represented by formula (I) wherein m, n and o are as defined above and:

(1) R1 represents an unsubstituted 4-pyridine ring or 4-pyrimidine ring; and/or (2) R2 represents a benzene ring or a naphthalene; the ring being optionally substituted by 1 to 4 substituents selected from a $C_{1-3}$ alkyl group, a $C_{1-2}$ perhalogenated alkyl group, a $C_{3-4}$ cycloalkyl group, a $C_{3-4}$ cycloalkyl-$C_{1-3}$ alkyl group, a halogen atom, a hydroxyl group, a nitro, a cyano, an amino, a $C_{1-3}$ alkoxy group optionally substituted by a $C_{3-4}$ cycloalkyl group, a $C_{1-2}$ perhalogenated alkoxy group or a $C_{1-3}$ alkylsulfonyl group; and/or
(3) R3 represents a hydrogen atom or a halogen atom; and/or
(4) R4 represents a hydrogen atom; and/or
(5) R5 represents a hydrogen atom; and/or
(6) R6 represents a hydrogen atom, a $C_{1-6}$ alkyl group;
(7) R7 represents a hydrogen atom; and/or
(8) Y represents two hydrogen atoms, or an oxygen atom; and/or
(9) Z represents a bond, an oxygen atom, a nitrogen atom substituted by a hydrogen atom; and/or
(10) n represents 0 to 1; and/or
(11) m represents 0 to 1 and o represents 1 to 2; and more particularly wherein R1, R2, R3, R4, R5, R6, R7, m, n, o, Y and Z are as defined here-above.

A further object of the present invention includes the group of compounds of table 1 of formula as defined hereunder:
1. (+/−) N-(4-Oxo-2-pyrimidin-4-yl-6,7,8,9-tetrahydro-4H-pyrido[1,2-a]pyrimidin-9-yl)benzamide
2. (+/−) 2-Methoxy-N-(4-oxo-2-pyridin-4-yl-6,7,8,9-tetrahydro-4H-pyrido[1,2-a]pyrimidin-9-yl)benzamide
3. (+/−) N-(4-Oxo-2-pyridin-4-yl-6,7,8,9-tetrahydro-4H-pyrido[1,2-a]pyrimidin-9-yl)-2-phenylacetamide
4. (+/−) Phenyl (4-oxo-2-pyridin-4-yl-6,7,8,9-tetrahydro-4H-pyrido[1,2-a]pyrimidin-9-yl)carbamate
5. (+/−) N-(4-Fluorophenyl)-N'-(4-oxo-2-pyrimidin-4-yl-6,7,8,9-tetrahydro-4H-pyrido[1,2-a]pyrimidin-9-yl)urea
6. (+/−) N-(4-Oxo-2-pyridin-4-yl-6,7,8,9-tetrahydro-4H-pyrido[1,2-a]pyrimidin-9-yl)-N'-phenylurea
7. (+/−) 9-[(2-Methoxybenzyl)amino]-2-pyridin-4-yl-6,7,8,9-tetrahydro-4H-pyrido[1,2-a]pyrimidin-4-one
8. (+/−) 3-Fluoro-N-(4-oxo-2-pyrimidin-4-yl-6,7,8,9-tetrahydro-4H-pyrido[1,2-a]pyrimidin-9-yl)benzamide
9. (+/−) 4-Isopropoxy-N-(4-oxo-2-pyridin-4-yl-6,7,8,9-tetrahydro-4H-pyrido[1,2-a]pyrimidin-9-yl)benzamide
10. (+/−) 2-Chloro-N-(4-oxo-2-pyridin-4-yl-6,7,8,9-tetrahydro-4H-pyrido[1,2-a]pyrimidin-9-yl)benzamide
11. (+/−) 4-Fluoro-N-(4-oxo-2-pyridin-4-yl-6,7,8,9-tetrahydro-4H-pyrido[1,2-a]pyrimidin-9-yl)benzamide
12. (+/−) 3-Cyano-N-(4-oxo-2-pyridin-4-yl-6,7,8,9-tetrahydro-4H-pyrido[1,2-a]pyrimidin-9-yl)benzamide
13. (+/−) 2-Chloro-5-fluoro-N-(4-oxo-2-pyridin-4-yl-6,7,8,9-tetrahydro-4H-pyrido[1,2-a]pyrimidin-9-yl)benzamide
14. (+/−) 2-Methoxy-N-(4-oxo-2-pyrimidin-4-yl-6,7,8,9-tetrahydro-4H-pyrido[1,2-a]pyrimidin-9-yl)benzamide
15. (+/−) 4-Fluoro-N-(4-oxo-2-pyrimidin-4-yl-6,7,8,9-tetrahydro-4H-pyrido[1,2-a]pyrimidin-9-yl)-2-(trifluoromethyl)benzamide
16. (+/−) 4-Methoxy-N-(4-oxo-2-pyridin-4-yl-6,7,8,9-tetrahydro-4H-pyrido[1,2-a]pyrimidin-9-yl)-3-(trifluoromethyl)benzamide
17. (+/−) N-(4-Oxo-2-pyridin-4-yl-6,7,8,9-tetrahydro-4H-pyrido[1,2-a]pyrimidin-9-yl)-2-(trifluoromethyl)benzamide
18. (+/−) 2-Chloro-4-fluoro-5-nitro-N-(4-oxo-2-pyridin-4-yl-6,7,8,9-tetrahydro-4H-pyrido[1,2-a]pyrimidin-9-yl)benzamide
19. (+/−) N-(4-Oxo-2-pyridin-4-yl-6,7,8,9-tetrahydro-4H-pyrido[1,2-a]pyrimidin-9-yl)-2-naphthamide
20. (+/−) 3-Chloro-N-(4-oxo-2-pyridin-4-yl-6,7,8,9-tetrahydro-4H-pyrido[1,2-a]pyrimidin-9-yl)benzamide
21. (+/−) 2,6-Dimethoxy-N-(4-oxo-2-pyrimidin-4-yl-6,7,8,9-tetrahydro-4H-pyrido[1,2-a]pyrimidin-9-yl)benzamide
22. (+/−) 3-Methoxy-N-(4-oxo-2-pyrimidin-4-yl-6,7,8,9-tetrahydro-4H-pyrido[1,2-a]pyrimidin-9-yl)benzamide
23. (+/−) 2-Fluoro-6-methoxy-N-(4-oxo-2-pyrimidin-4-yl-6,7,8,9-tetrahydro-4H-pyrido[1,2-a]pyrimidin-9-yl)benzamide
24. (+/−) 4-Fluoro-2-methoxy-N-(4-oxo-2-pyridin-4-yl-6,7,8,9-tetrahydro-4H-pyrido[1,2-a]pyrimidin-9-yl)benzamide
25. (+/−) 4-Chloro-2-methoxy-N-(4-oxo-2-pyrimidin-4-yl-6,7,8,9-tetrahydro-4H-pyrido[1,2-a]pyrimidin-9-yl)benzamide
26. (+/−) 2-Ethoxy-N-(4-oxo-2-pyridin-4-yl-6,7,8,9-tetrahydro-4H-pyrido[1,2-a]pyrimidin-9-yl)benzamide
27. (+/−) N-(3-Bromo-4-oxo-2-pyridin-4-yl-6,7,8,9-tetrahydro-4H-pyrido[1,2-a]pyrimidin-9-yl)-2-methoxybenzamide
28. (+/−) 4-Amino-5-chloro-2-methoxy-N-(4-oxo-2-pyridin-4-yl-6,7,8,9-tetrahydro-4H-pyrido[1,2-a]pyrimidin-9-yl)benzamide
29. (+/−) N-(4-Oxo-2-pyridin-4-yl-6,7,8,9-tetrahydro-4H-pyrido[1,2-a]pyrimidin-9-yl)-2-(trifluoromethoxy)benzamide
30. (+/−) 2-Isopropoxy-N-(4-oxo-2-pyridin-4-yl-6,7,8,9-tetrahydro-4H-pyrido[1,2-a]pyrimidin-9-yl)benzamide
31. (+/−) 2-(Cyclopropylmethoxy)-N-(4-oxo-2-pyridin-4-yl-6,7,8,9-tetrahydro-4H-pyrido[1,2-a]pyrimidin-9-yl)benzamide
32. (+/−) 4-Amino-5-chloro-2-methoxy-N-(4-oxo-2-pyrimidin-4-yl-6,7,8,9-tetrahydro-4H-pyrido[1,2-a]pyrimidin-9-yl)benzamide
33. (+/−) 4-Fluoro-2-methoxy-N-(4-oxo-2-pyrimidin-4-yl-6,7,8,9-tetrahydro-4H-pyrido[1,2-a]pyrimidin-9-yl)benzamide
34. (+/−) 2-(Cyclopropylmethoxy)-N-(4-oxo-2-pyrimidin-4-yl-6,7,8,9-tetrahydro-4H-pyrido[1,2-a]pyrimidin-9-yl)benzamide
35. (+/−) N-(4-Oxo-2-pyrimidin-4-yl-6,7,8,9-tetrahydro-4H-pyrido[1,2-a]pyrimidin-9-yl)-2-naphthamide
36. (+/−) 3-Chloro-N-(4-oxo-2-pyrimidin-4-yl-6,7,8,9-tetrahydro-4H-pyrido[1,2-a]pyrimidin-9-yl)benzamide
37. (+/−) 5-Chloro-2-methoxy-N-(4-oxo-2-pyrimidin-4-yl-6,7,8,9-tetrahydro-4H-pyrido[1,2-a]pyrimidin-9-yl)benzamide
38. (+/−) 4-Amino-2-methoxy-N-(4-oxo-2-pyrimidin-4-yl-6,7,8,9-tetrahydro-4H-pyrido[1,2-a]pyrimidin-9-yl)benzamide
39. (+/−) 2-Methoxy-N-(4-oxo-2-pyrimidin-4-yl-6,7,8,9-tetrahydro-4H-pyrido[1,2-a]pyrimidin-9-yl)-4-trifluoromethyl-benzamide
40. (+/−) 5-(Ethylsulfonyl)-2-methoxy-N-(4-oxo-2-pyrimidin-4-yl-6,7,8,9-tetrahydro-4H-pyrido[1,2-a]pyrimidin-9-yl)benzamide
41. (+/−) 2,3-Dimethoxy-N-(4-oxo-2-pyrimidin-4-yl-6,7,8,9-tetrahydro-4H-pyrido[1,2-a]pyrimidin-9-yl)benzamide
42. (−) 4-Chloro-2-methoxy-N-(4-oxo-2-pyrimidin-4-yl-6,7,8,9-tetrahydro-4H-pyrido[1,2-a]pyrimidin-9-yl)benzamide
43. (+) 4-Chloro-2-methoxy-N-(4-oxo-2-pyrimidin-4-yl-6,7,8,9-tetrahydro-4H-pyrido[1,2-a]pyrimidin-9-yl)benzamide
44. (+/−) 5-Bromo-2-methoxy-N-(4-oxo-2-pyrimidin-4-yl-6,7,8,9-tetrahydro-4H-pyrido[1,2-a]pyrimidin-9-yl)benzamide 45. (+/−) 2-{[(4-Oxo-2-pyrimidin-4-yl-6,7,8,9-tetrahydro-4H-pyrido[1,2-a]pyrimidin-9-yl)amino]carbonyl}phenyl acetate
46. (+/−) 2-Hydroxy-N-(4-oxo-2-pyrimidin-4-yl-6,7,8,9-tetrahydro-4H-pyrido[1,2-a]pyrimidin-9-yl)benzamide
47. (+/−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide
48. (+) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide
49. (−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide
50. (+/−) 4-Chloro-2-methoxy-N-methyl-N-(4-oxo-2-pyrimidin-4-yl-6,7,8,9-tetrahydro-4H-pyrido[1,2-a]pyrimidin-9-yl)benzamide
51. (+) 4-Fluoro-2-methoxy-N-(4-oxo-2-pyrimidin-4-yl-6,7,8,9-tetrahydro-4H-pyrido[1,2-a]pyrimidin-9-yl)benzamide
52. (−) 4-Fluoro-2-methoxy-N-(4-oxo-2-pyrimidin-4-yl-6,7,8,9-tetrahydro-4H-pyrido[1,2-a]pyrimidin-9-yl)benzamide
53. (+/−) 5-Chloro-2-methoxy-N-(9-methyl-4-oxo-2-pyrimidin-4-yl-6,7,8,9-tetrahydro-4H-pyrido[1,2-a]pyrimidin-9-yl)-benzamide
54. (+/−) 4-Fluoro-2-methoxy-N-(9-methyl-4-oxo-2-pyrimidin-4-yl-6,7,8,9-tetrahydro-4H-pyrido[1,2-a]pyrimidin-9-yl)-benzamide
55. (+/−) 4-Amino-5-chloro-2-methoxy-N-(9-methyl-4-oxo-2-pyrimidin-4-yl-6,7,8,9-tetrahydro-4H-pyrido[1,2-a]pyrimidin-9-yl)-benzamide
56. (+/−) 2-Methoxy-N-(9-methyl-4-oxo-2-pyrimidin-4-yl-6,7,8,9-tetrahydro-4H-pyrido[1,2-a]pyrimidin-9-yl)-4-trifluoromethyl-benzamide
57. (+/−) 2-Fluoro-6-methoxy-N-(9-methyl-4-oxo-2-pyrimidin-4-yl-6,7,8,9-tetrahydro-4H-pyrido[1,2-a]pyrimidin-9-yl)-benzamide
58. (+/−) 2-Methoxy-N-(9-methyl-4-oxo-2-pyrimidin-4-yl-6,7,8,9-tetrahydro-4H-pyrido[1,2-a]pyrimidin-9-yl)-benzamide
59. (+/−) 5-Bromo-2-methoxy-N-(9-methyl-4-oxo-2-pyrimidin-4-yl-6,7,8,9-tetrahydro-4H-pyrido[1,2-a]pyrimidin-9-yl)-benzamide
60. (+/−)-4-Dimethylamino-2-methoxy-N-(9-methyl-4-oxo-2-pyrimidin-4-yl-6,7,8,9-tetrahydro-4H-pyrido[1,2-a]pyrimidin-9-yl)-benzamide
61. (+/−)-2,4-Dimethoxy-N-(9-methyl-4-oxo-2-pyrimidin-4-yl-6,7,8,9-tetrahydro-4H-pyrido[1,2-a]pyrimidin-9-yl)-benzamide A further object of the present invention includes the group of compounds of table 2 of formula as defined hereunder:
1. (+/−) 4-Chloro-2-methoxy-N-(4-oxo-2-pyrimidin-4-yl-4,6,7,8-tetrahydro-pyrrolo[1,2-a]pyrimidin-8-yl)-benzamide
2. (+/−) 4-Fluoro-2-methoxy-N-(4-oxo-2-pyrimidin-4-yl-4,6,7,8-tetrahydro-pyrrolo[1,2-a]pyrimidin-8-yl)-benzamide
3. (+/−) 4-Amino-5-chloro-2-methoxy-N-(4-oxo-2-pyrimidin-4-yl-4,6,7,8-tetrahydro-pyrrolo[1,2-a]pyrimidin-8-yl)-benzamide
4. (+/−) 5-Chloro-2-methoxy-N-(4-oxo-2-pyrimidin-4-yl-4,6,7,8-tetrahydro-pyrrolo[1,2-a]pyrimidin-8-yl)-benzamide
5. (+/−) 4-Chloro-2-methoxy-N-(4-oxo-2-pyridin-4-yl-4,6,7,8-tetrahydro-pyrrolo[1,2-a]pyrimidin-8-yl)-benzamide.
6. (+/−) 4-Fluoro-2-methoxy-N-(4-oxo-2-pyridin-4-yl-4,6,7,8-tetrahydro-pyrrolo[1,2-a]pyrimidin-8-yl)-benzamide.

A further object of the present invention includes the group of compounds of table 3 of formula as defined hereunder:
1. (+/−) 4-Chloro-2-methoxy-N-(4-oxo-2-pyrimidin-4-yl-4,6,7,8,9,10-hexahydropyrimido[1,2-a]azepin-10-yl)benzamide
2. (+/−) 4-Fluoro-2-methoxy-N-(4-oxo-2-pyrimidin-4-yl-4,6,7,8,9,10-hexahydropyrimido[1,2-a]azepin-10-yl)benzamide
3. (+/−) 5-Chloro-2-methoxy-N-(4-oxo-2-pyrimidin-4-yl-4,6,7,8,9,10-hexahydropyrimido[1,2-a]azepin-10-yl)benzamide
4. (+/−) 4-Amino-5-chloro-2-methoxy-N-(4-oxo-2-pyrimidin-4-yl-4,6,7,8,9,10-hexahydropyrimido[1,2-a]azepin-10-yl)benzamide
5. (+/−) 4-Amino-2-methoxy-N-(4-oxo-2-pyrimidin-4-yl-4,6,7,8,9,10-hexahydropyrimido[1,2-a]azepin-10-yl)benzamide
6. (+/−) 2-Methoxy-N-(4-oxo-2-pyrimidin-4-yl-4,6,7,8,9,10-hexahydropyrimido[1,2-a]azepin-10-yl)benzamide
7. (+/−) 5-(Aminosulfonyl)-2-methoxy-N-(4-oxo-2-pyrimidin-4-yl-4,6,7,8,9,10-hexahydropyrimido[1,2-a]azepin-10-yl)benzamide
8. (+/−) 2-Hydroxy-N-(4-oxo-2-pyrimidin-4-yl-4,6,7,8,9,10-hexahydropyrimido[1,2-a]azepin-10-yl)benzamide
9. (+/−) 5-Bromo-2-methoxy-N-(4-oxo-2-pyrimidin-4-yl-4,6,7,8,9,10-hexahydropyrimido[1,2-a]azepin-10-yl)benzamide
10. (+/−) 2,4-Dimethoxy-N-(4-oxo-2-pyrimidin-4-yl-4,6,7,8,9,10-hexahydropyrimido[1,2-a]azepin-10-yl)benzamide
11. (+/−) 2-{[(4-Oxo-2-pyrimidin-4-yl-4,6,7,8,9,10-hexahydropyrimido[1,2-a]azepin-10-yl)amino]carbonyl}phenyl acetate
12. (+/−) 2,3-Dimethoxy-N-(4-oxo-2-pyrimidin-4-yl-4,6,7,8,9,10-hexahydropyrimido[1,2-a]azepin-10-yl)benzamide
13. (+/−) 2-Methoxy-N-(4-oxo-2-pyrimidin-4-yl-4,6,7,8,9,10-hexahydropyrimido[1,2-a]azepin-10-yl)-5-(trifluoromethoxy)benzamide
14. (+/−) 2,5-Dimethoxy-N-(4-oxo-2-pyrimidin-4-yl-4,6,7,8,9,10-hexahydropyrimido[1,2-a]azepin-10-yl)benzamide
15. (+) 4-Fluoro-2-methoxy-N-(4-oxo-2-pyrimidin-4-yl-4,6,7,8,9,10-hexahydropyrimido[1,2-a]azepin-10-yl)benzamide
16. (−) 4-Fluoro-2-methoxy-N-(4-oxo-2-pyrimidin-4-yl-4,6,7,8,9,10-hexahydropyrimido[1,2-a]azepin-10-yl)benzamide
17. (+/−) 4-Chloro-2-methoxy-N-(4-oxo-2-pyridin-4-yl-4,6,7,8,9,10-hexahydropyrimido[1,2-a]azepin-10-yl)benzamide
18. (+/−) 5-Bromo-2-methoxy-N-(4-oxo-2-pyridin-4-yl-4,6,7,8,9,10-hexahydropyrimido[1,2-a]azepin-10-yl)benzamide
19. (+/−) 4-Fluoro-2-methoxy-N-(4-oxo-2-pyridin-4-yl-4,6,7,8,9,10-hexahydropyrimido[1,2-a]azepin-10-yl)benzamide
20. (+/−) 2-Methoxy-N-(4-oxo-2-pyridin-4-yl-4,6,7,8,9,10-hexahydropyrimido[1,2-a]azepin-10-yl)benzamide
21. (+/−) 5-Chloro-2-methoxy-N-(4-oxo-2-pyridin-4-yl-4,6,7,8,9,10-hexahydropyrimido[1,2-a]azepin-10-yl)benzamide 22. (+/−) 4-Amino-2-methoxy-N-(4-oxo-2-pyridin-4-yl-4,6,7,8,9,10-hexahydropyrimido[1,2-a]azepin-10-yl)benzamide
23. (+/−) 2-{[(4-Oxo-2-pyridin-4-yl-4,6,7,8,9,10-hexahydropyrimido[1,2-a]azepin-10-yl)amino]carbonyl}phenyl acetate
24. (+/−) 2,4-Dimethoxy-N-(4-oxo-2-pyridin-4-yl-4,6,7,8,9,10-hexahydropyrimido[1,2-a]azepin-10-yl)benzamide
25. (+) 4-Chloro-2-methoxy-N-(4-oxo-2-pyrimidin-4-yl-4,6,7,8,9,10-hexahydropyrimido[1,2-a]azepin-10-yl)benzamide
26. (−) 4-Chloro-2-methoxy-N-(4-oxo-2-pyrimidin-4-yl-4,6,7,8,9,10-hexahydropyrimido[1,2-a]azepin-10-yl)benzamide As a further object, the present invention concerns also methods for preparing the pyrimidone compounds represented by the aforementioned formula (I).

These compounds can be prepared, for example, according to methods explained below.

Preparation Method

Pyrimidone compounds represented by the aforementioned formula (I), may be prepared according to the method described in the scheme 1.

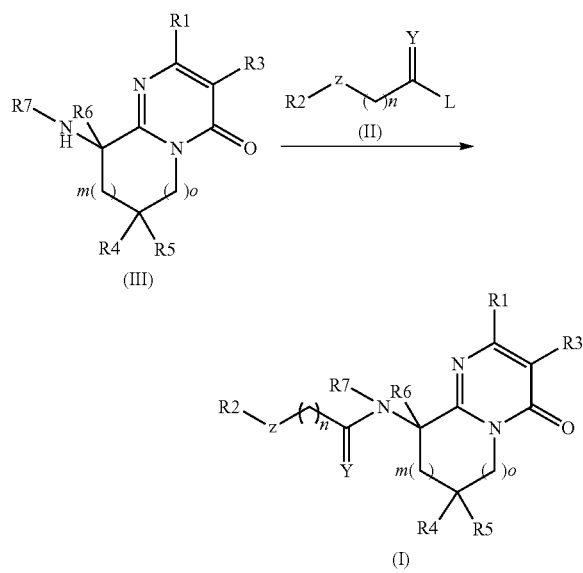

Scheme 1

(In the above scheme the definition of R1, R2, R3, R4, R5, R6, R7, m, n, o, Y and Z are the same as those already described for compound of formula (I)).

Following this method, the pyrimidone derivative represented by the above formula (III), wherein R1, R3, R4, R5, R6, R7, m and o are as defined for compound of formula (I), is allowed to react with a base such as triethylamine, sodium carbonate or potassium carbonate in a solvent such as tetrahydrofuran, N-methylpyrrolidone, N,N-dimethylacetamide or chloroform at a suitable temperature ranging from 0 to 130° C. under ordinary air, then with a compound of formula (II), wherein R2, Z, Y and n are as defined for compound of formula (I) and L represents a leaving group preferably chlorine, bromide or mesyl group, to obtain the compound of the aforementioned formula (I).

Alternatively compounds of formula (I) wherein Y represents two hydrogen atoms may be prepared by reductive amination of a compound of formula (II) wherein Y represents an oxygen atom and L represents a hydrogen atom, by a compound of formula (III) wherein R1, R3, R4, R5, R6, m and o are as defined for compound of formula (I) and R7 is a hydrogen, according to well known methods to one skilled in the art.

Compound of formula (II) is commercially available or may be synthesized according to well-known methods to one skilled in the art.

Compound of formula (III) may be prepared according to the method defined in scheme 2.

Scheme 2

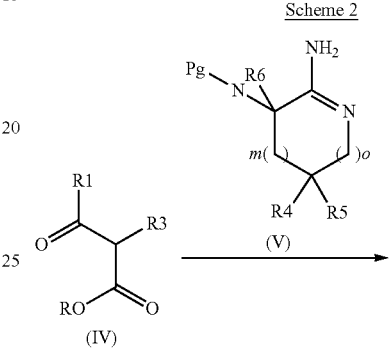

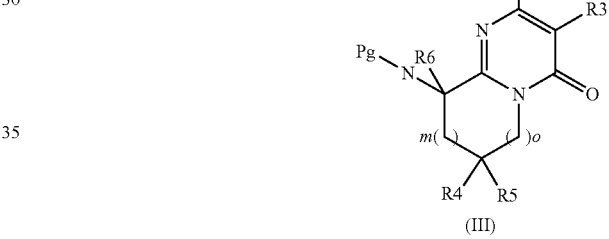

(In the above scheme the definition of R1, R2, R3, R4, R5, R6, m and o are the same as already described.)

According to this method, the 3-ketoester of formula (IV), wherein R1 and R3 are as defined for compound of formula (I), R is an alkyl group such as for example methyl or ethyl, is allowed to react with a compound of formula (V) wherein R4, R5, R6, m and o are as defined for compound of formula (I) and Pg is a suitable protecting group such as for example a phthalimido group. The reaction may be carried out in the presence of a base such as potassium carbonate, in an alcoholic solvent such as methanol, ethanol and the like or without, at a suitable temperature ranging from 25° to 140° C. under ordinary air.

Additionally compound of formula (III) wherein R3 represents a hydrogen atom may be halogenated in order to give compounds of formula (III) wherein R3 is a halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (IV) wherein R3 represents a fluorine atom may be obtained by analogy to the method described in Tetrahedron Letters, Vol. 30, No. 45, pp 6113-6116, 1989.

In addition, compounds of formula (IV) wherein R3 represents a hydrogen atom may be obtained by analogy to the method described in patent DE 2705582.

As a further object, the present invention concerns also the compounds of formula (III) as intermediates of compounds of formula (I).

Compound of formula (IV) is commercially available or may be synthesized according to well-known methods to one skilled in the art.

For example compounds of formula (IV), wherein R1 represent a pyridine ring or a pyrimidine ring, optionally substituted by a $C_{1-16}$ alkyl group, $C_{1-6}$ alkoxy group or a halogen atom, can be prepared by reacting respectively an isonicotinic acid or a pyrimidine-carboxylic acid, optionally substituted by a $C_{1-6}$ alkyl group, $C_{1-6}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compound of formula (V) may be synthesized according to well-known methods of one skilled in the art.

For example compound of formula (V), wherein m, o, R4, R5 and R6 are as defined for compound of formula (I) and a suitable protecting group Pg such as for example a phthalimido group, may be prepared according to the method defined in scheme 3, starting from compound of formula (VI). The conditions which may be used are given in the chemical examples.

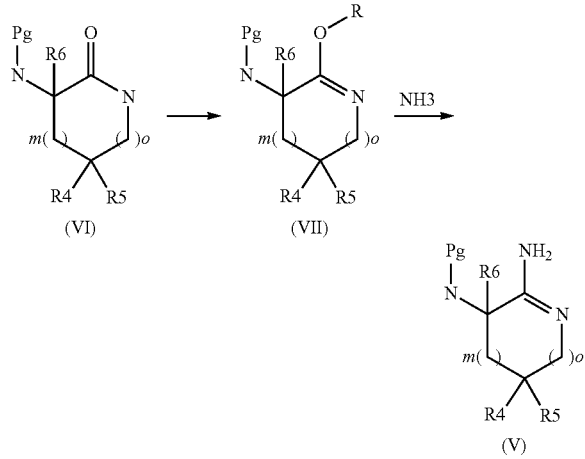

Scheme 3

Compound of formula (VI) may be synthesized by analogy to the method described in Heterocycles (1996), 42(2), 537-42, Enantiomer (2001), 6(5), 275-279, Synthesis (1991), (5), 417-20, Liebigs Annalen der Chemie (1987), (7), 647-8. Archiv der Pharmazie (Weinheim, Germany) (1989), 322(8), 499-505.

Compound of formula (VII) and formula (V) may be synthesized according to the method described in WO96/14844.

In the above reactions protection or deprotection of a functional group may sometimes be necessary. A suitable protecting group Pg can be chosen depending on the type of the functional group, and a method described in the literature may be applied. Examples of protecting groups, of protection and deprotection methods are given for example in Protective groups in Organic Synthesis Greene et al., 3rd Ed. (John Wiley & Sons, Inc., New York) 1999.

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, taupathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis, peripheral neuropathies; retinopathies and glaucoma; and other diseases such as non-insulin dependent diabetes (such as diabetes type II) and obesity; malaria, manic depressive illness; schizophrenia; alopecia; cancers such as colorectal, prostate breast cancer, non-small cell lung carcinoma, thyroid cancer, T or B-cell leukemia, several virus-induced tumors and in bone related pathologies. The medicament could also find an application in regenerative medicine The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound No. 2 of Table 1

(+/−) 2-Methoxy-N-(4-oxo-2-pyridin-4-yl-6,7,8,9-tetrahydro-4H-pyrido[1,2-a]pyrimidin-9-yl)benzamide 1.1 (+/−) 2-(2-Methoxy-3,4,5,6-tetrahydropyridin-3-yl)-1H-isoindole-1,3(2H)-dione To a solution of 13.474 g (91.1 mmol) of trimethyloxonium tetrafluoroborate in 294 mL of anhydrous dichloromethane was added 22.25 g (91.1 mmol) of (+/−)-3-phtalimidopiperidin-2-one (Heterocycles (1996), 42(2), 537-42, Enantiomer (2001), 6(5), 275-279, Synthesis (1991), (5), 417-20) and the resulting mixture was stirred at room temperature for 12 h. The mixture was hydrolyzed with a saturated aqueous solution of sodium hydrogen carbonate, extracted with dichloromethane, dried over sodium sulfate and the solvent was evaporated to afford 23.22 g (99%) of pure product as a yellow oil. The compound was used as such in the next step.

$^1$H NMR (CDCl$_3$; 200 MHz)

δ (ppm): 7.92-7.66 (m, 4H); 4.87-4.69 (m, 1H); 3.74-3.60 (m, 2H); 3.56 (s, 3H); 2.40-1.62 (m, 4H).

1.2 (+/−) 2-(2-Amino-3,4,5,6-tetrahydropyridin-3-yl)-1H-isoindole-1,3(2H)-dione hydrochloride (1:1).

To a solution of 23.224 g (89.92 mmol) of (+/−)2-(2-methoxy-3,4,5,6-tetrahydropyridin-3-yl)-1H-isoindole-1,3(2H)-dione dissolved in 409 mL of methanol was added at room temperature 4.81 g (89.92 mmol) of ammonium chloride. The resulting mixture was stirred under reflux for 12 h. The cooled solution was evaporated to remove solvent. The residue was triturated with diethyl ether and filtered to afford 23.8 g (95%) of the pure product as a white powder.

Mp: 242-244° C.

$^1$H NMR (DMSO-d$_6$; 200 MHz)

δ (ppm): 8.92 (br s, 2H); 8.02-7.85 (m, 4H); 5.28 (t, 1H); 3.58-3.12 (m, 2H); 2.15-1.78 (m, 4H).

1.3 (+/−) 2-(4-Oxo-2-pyridin-4-yl-6,7,8,9-tetrahydro-4H-pyrido[1,2-a]pyrimidin-9-yl)-1H-isoindole-1,3(2H)-dione To a suspension of 9.166 g (32.77 mmol) of (+/−) 2-(2-Amino-3,4,5,6-tetrahydropyridin-3-yl)-1H-isoindole-1,3 (2H)-dione hydrochloride (1:1) in 50 mL of toluene was added sodium methanolate (freshly prepared from 0.754 g (32.77 mmol) of sodium in 10 mL of methanol and the reaction mixture was stirred at room temperature for 1 h. The mixture was evaporated to dryness, dissolved in 50 mL of toluene and 4.87 g (25.21 mmol) of ethyl 3-(pyridin-4-yl)-3-oxopropionate was added. The resulting solution was stirred under reflux for 12 h. The cooled solution was evaporated to remove solvent. The mixture was dissolved in dichloromethane, washed with a saturated aqueous solution of ammonium chloride, saturated aqueous sodium chloride, dried over sodium sulfate and evaporated to dryness. The residue was chromatographed on silica gel eluting with a mixture of dichloromethane/methanol/aqueous ammonia solution (29%) in the proportions 97/3 10.3 led to afford 3.2 g (34%) of the desired compound as a white powder.

Mp: 211-213° C.

$^1$H NMR (DMSO-d$_6$; 200 MHz)

δ (ppm): 8.50 (d, 2H); 8.09-7.78 (m, 4H); 7.60 (d, 2H); 7.08 (s, 1H); 5.60-5.39 (m, 1H); 4.28-4.06 (m, 1H); 3.88-3.65 (m, 1H); 2.55-2.08 (m, 4H).

1.4 (+/−) 9-Amino-2-pyridin-4-yl-6,7,8,9-tetrahydro-4H-pyrido[1,2-a]pyrimidin-4-one To a solution of 3.2 g (8.59 mmol) of (+/−) 2-(4-oxo-2-pyridin-4-yl-6,7,8,9-tetrahydro-4H-pyrido[1,2-a]pyrimidin-9-yl)-1H-isoindole-1,3(2H)-dione dissolved in 24 mL of ethanol was added 2.09 mL (43 mmol) of hydrazine hydrate and the resulting mixture was stirred under reflux for 2 hours. The mixture was filtered and the solid obtained was triturated with dichloromethane for 24 h, filtered, and the resulting filtrates were evaporated to dryness. The resulting residue was purified on silica gel eluting with a mixture of dichloromethane/methanol in the proportions 98/2 to 96/4 to give 1.37 g (66%) of the desired compound as a brown powder.

Mp: 144-146° C.

$^1$H NMR (CDCl$_3$; 200 MHz)

δ (ppm): 8.77 (d, 2H); 7.85 (d, 2H); 6.89 (s, 1H); 4.26-3.91 (m, 3H); 2.48-1.61 (m, 6H).

1.5 (+/−) 2-Methoxy-N-(4-oxo-2-pyridin-4-yl-6,7,8,9-tetrahydro-4H-pyrido[1,2-a]pyrimidin-9-yl)benzamide To a solution of 0.080 g (0.33 mmol) of (+/−) 9-amino-2-pyridin-4-yl-6,7,8,9-tetrahydro-4H-pyrido[1,2-a]pyrimidin-4-one dissolved in 2.2 mL of tetrahydrofuran was added 60 μl (0.40 mmol) of triethylamine and 50 μl (0.40 mmol) of 2-methoxy-benzoyl chloride. The resulting mixture was stirred at room temperature for 1 h.

Water was added and the mixture extracted with dichloromethane. The extracts were washed with a saturated aqueous solution of ammonium chloride, dried and evaporated. The residue was triturated with diethyl ether and filtered to afford 0.105 g (84%) of the pure product as a yellow powder.

Mp: 155-157° C.

$^1$H NMR (CDCl$_3$; 200 MHz)

δ (ppm): 9.26 (br s, 1H); 8.76 (d, 2H); 8.30 (d, 1H); 7.88 (d, 2H); 7.52 (t, 1H); 7.22-7.03 (m, 2H); 6.92 (s, 1H); 5.26-5.08 (m, 1H); 4.55 (dt, 1H); 3.93 (s, 3H); 3.92-3.71 (m, 1H); 3.08-2.85 (m, 1H); 2.38-1.94 (m, 2H); 1.78-1.53 (m, 1H).

Example 2

Compound No. 7 of Table 1

(+/−) 9-[(2-Methoxybenzyl)amino]-2-pyridin-4-yl-6,7,8,9-tetrahydro-4H-pyrido[1,2-a]pyrimidin-4-one hydrochloride (2:1).

To a solution of 0.080 g (0.33 mmol) of (+/−) 9-amino-2-pyridin-4-yl-6,7,8,9-tetrahydro-4H-pyrido[1,2-a]pyrimidin-4-one in 2 ml of toluene was added 0.045 g (0.33 mmol) of 2-methoxybenzaldehyde and the resulting solution was refluxed for 3 h in a Dean-Stark apparatus.

The resulting mixture was dried over sodium sulfate, filtered and evaporated. The residue was dissolved in 2 mL of methanol, pH was adjusted to 6 with acetic acid and 0.042 g (0.66 mmol) of sodium cyanoborohydride was added. The resulting mixture was stirred at room temperature for 1 h. The reaction mixture was concentrated, the residue was dissolved in dichloromethane, washed with a saturated aqueous solution of ammonium chloride, saturated aqueous solution of sodium chloride, dried over sodium sulfate and evaporated. The base was transformed into its hydrochloride salt to give 0.081 g of pure product.

Mp: 230-232° C.

$^1$H NMR (DMSO-d$_6$; 200 MHz)

δ (ppm): 9.76 (br s, 1H); 8.90 (d, 2H); 8.50 (d, 2H); 7.60-7.29 (m, 2H); 7.38 (s, 1H); 7.13-6.88 (m, 2H); 4.70-4.49 (m, 1H); 4.36 (dd, 2H); 4.06-3.65 (m, 2H); 3.72 (s, 3H); 2.70-1.87 (m, 4H).

Example 3

Compound No. 6 of Table 1

(+/−) N-(4-Oxo-2-pyridin-4-yl-6,7,8,9-tetrahydro-4H-pyrido[1,2-a]pyrimidin-9-yl)-N'-phenylurea To a solution of 0.07 g (0.29 mmol) of (+/−) 9-amino-2-pyridin-4-yl-6,7,8,9-tetrahydro-4H-pyrido[1,2-a]pyrimidin-4-one dissolved in 1 mL of dichloromethane at 10° C. was added 0.034 g (0.29 mmol) of phenylisocyanate dissolved in 1 mL at 10° C. The resulting mixture was stirred at 10° C. for 30 min. The mixture was stirred at room temperature for 1 h.

The reaction mixture was concentrated, and the residue was chromatographed on silica gel eluting with a mixture of dichloromethane/methanol/aqueous ammonia solution (29%) in the proportions 90/10/1. The residue was triturated with diethyl ether and filtered to afford 0.088 g (84%) of the pure product as a brown powder.

Mp: 254-256° C.

$^1$H NMR (DMSO-d$_6$; 200 MHz)

δ (ppm): 8.90 (br s, 1H); 8.61 (d, 2H); 8.03 (d, 2H); 7.43 (d, 2H); 7.27 (t, 2H); 7.11 (s, 1H); 6.92 (t, 1H); 6.72 (br s, 1H); 4.95-4.78 (m, 1H); 4.17-3.73 (m, 2H); 2.39-2.18 (m, 1H); 2.13-1.60 (m, 3H).

Example 4

Compound No. 4 of Table 1

(+/−) Phenyl (4-oxo-2-pyridin-4-yl-6,7,8,9-tetrahydro-4H-pyrido[1,2-a]pyrimidin-9-yl)carbamate To a solution of 0.07 g (0.29 mmol) of (+/−) 9-amino-2-pyridin-4-yl-6,7,8,9-tetrahydro-4H-pyrido[1,2-a]pyrimidin-4-one dissolved in 4 mL of tetrahydrofuran at 0° C. was added 29.2 µl (0.29 mmol) of triethylamine and 50 µl (0.32 mmol) of phenylchloroformate. The resulting mixture was stirred at 0° C. for 45 min and warmed at room temperature for 16 h.

A saturated aqueous solution of ammonium chloride was added and the reaction mixture extracted with ethyl acetate. The extracts were dried and evaporated. The residue was triturated with diethyl ether and filtered to afford 0.068 g (65%) of the pure product as a white powder.

Mp: 193-195° C.

$^1$H NMR (CDCl$_3$; 200 MHz)

δ (ppm): 8.72 (d, 2H); 8.22 (br s, 1H); 8.04 (d, 2H); 7.50-7.35 (m, 2H); 7.30-7.08 (m, 3H); 7.12 (s, 1H); 4.89-4.70 (m, 1H); 3.92 (t, 2H); 2.35-1.80 (m, 4H).

Example 5

Compound No. 14 of Table 1

(+/−)2-Methoxy-N-(4-oxo-2-pyrimidin-4-yl-6,7,8,9-tetrahydro-4H-pyrido[1,2-a]pyrimidin-9-yl)benzamide 5.1 (+/−) 2-(4-Oxo-2-pyrimidin-4-yl-6,7,8,9-tetrahydro-4H-pyrido[1,2-a]pyrimidin-9-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate, the compound was obtained as a white powder.

Mp.: 279.9-280.9° C.

$^1$H NMR (DMSO-d$_6$; 200 MHz)

δ (ppm): 9.21 (s, 1H); 8.75 (d, 1H); 8.01-7.81 (m, 4H); 7.52 (d, 1H); 7.19 (s, 1H); 5.58-5.40 (m, 1H); 4.26-4.09 (m, 1H); 3.89-3.68 (m, 1H); 2.48-2.02 (m, 4H.).

5.2 (+/−) 9-Amino-2-pyrimidin-4-yl-6,7,8,9-tetrahydro-4H-pyrido[1,2-a]pyrimidin-4-one By analogy with the method described in example 1 (step 1.4), using (+/−) 2-(4-oxo-2-pyrimidin-4-yl-6,7,8,9-tetrahydro-4H-pyrido[1,2-a]pyrimidin-9-yl)-1H-isoindole-1,3(2H)-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp: 111-113° C.

$^1$H NMR (DMSO-d$_6$; 200 MHz)

δ (ppm): 9.29 (s, 1H); 8.99 (d, 1H); 8.43 (d, 1H); 7.18 (s, 1H); 4.02-3.75 (m, 3H); 2.25 (br s; 2H); 2.23-1.75 (m, 3H); 1.74-1.48 (m, 1H).

5.3 (+/−)2-Methoxy-N-(4-oxo-2-pyrimidin-4-yl-6,7,8,9-tetrahydro-4H-pyrido[1,2-a]pyrimidin-9-yl)benzamide By analogy with the method described in example 1 (step 1.5), using (+/−) 9-amino-2-pyrimidin-4-yl-6,7,8,9-tetrahydro-4H-pyrido[1,2-a]pyrimidin-4-one in place of (+/−) 9-amino-2-pyridin-4-yl-6,7,8,9-tetrahydro-4H-pyrido[1,2-a]pyrimidin-4-one, the compound was obtained as a white powder.

Mp: 249-251° C.

$^1$H NMR (DMSO-d$_6$; 200 MHz)

δ (ppm): 9.30 (s, 1H); 9.02 (d, 1H); 8.96 (br s, 1H); 8.18 (d, 1H); 7.83 (d, 1H); 7.58-7.43 (m, 1H); 7.28-7.14 (m, 2H); 7.07 (t, 1H); 5.26-5.08 (m, 1H); 4.11-3.75 (m, 2H); 3.88 (s, 3H); 2.26-2.44 (m, 1H); 2.18-1.69 (m, 3H).

Example 6

Compound No. 42 of Table 1

(−) 4-Chloro-2-methoxy-N-(4-oxo-2-pyrimidin-4-yl-6,7,8,9-tetrahydro-4H-pyrido[1,2-a]pyrimidin-9-yl)benzamide 196 mg (0.476 mmol) of (+/−) 4-Chloro-2-methoxy-N-(4-oxo-2-pyrimidin-4-yl-6,7,8,9-tetrahydro-4H-pyrido[1,2-a]pyrimidin-9-yl)benzamide (compound No. 29 of table 1) was separated by chiral preparative HPLC (CHIRALCEL OD-I 20 μm 350×80 mm) eluting with a mixture of methanol/dichloromethane/diisopropylethylamine/heptane to give 95 mg of pure product obtained in the form of free base.

Mp: 174-176° C. $[α]_D^{20}$=−46.9° (c=0.387, DMSO).

$^1$H NMR (DMSO-d$_6$; 200 MHz)

δ (ppm): 9.40 (s, 1H); 9.15 (d, 1H); 9.05 (d, 1H); 8.25 (d, 1H); 7.90 (d, 1H); 7.35 (s, 1H); 7.3 (s, 1H); 7.15 (d, 1H); 5.20 (m, 1H); 4.11-3.85 (m, 2H); 3.35 (s, 3H); 2.44-1.80 (m, 4H).

Example 7

Compound No. 43 of Table 1

(+) 4-Chloro-2-methoxy-N-(4-oxo-2-pyrimidin-4-yl-6,7,8,9-tetrahydro-4H-pyrido[1,2-a]pyrimidin-9-yl)benzamide 196 mg (0.476 mmol) of (+/−) 4-Chloro-2-methoxy-N-(4-oxo-2-pyrimidin-4-yl-6,7,8,9-tetrahydro-4H-pyrido[1,2-a]pyrimidin-9-yl)benzamide (compound No. 29 of table 1) was separated by chiral preparative HPLC (CHIRALCEL OD-I 20 μm 350×80 mm) eluting with a mixture of methanol/dichloromethane/diisopropylethylamine/heptane to give 100 mg of pure product obtained in the form of free base.

Mp: 175-177° C. $[α]_D^{20}$=+42.5° (c=0.287, DMSO).

$^1$H NMR (DMSO-d$_6$; 200 MHz)

δ (ppm): 9.40 (s, 1H); 9.15 (d, 1H); 9.05 (d, 1H); 8.25 (d, 1H); 7.90 (d, 1H); 7.35 (s, 1H); 7.3 (s, 1H); 7.15 (d, 1H); 5.20 (m, 1H); 4.11-3.85 (m, 2H); 3.35 (s, 3H); 2.44-1.80 (m, 4H).

Example 8

Compound No. 1 of Table 2

(+/−) 4-Chloro-2-methoxy-N-(4-oxo-2-pyrimidin-4-yl-4,6,7,8-tetrahydro-pyrrolo[1,2-a]pyrimidin-8-yl)-benzamide

8.1 2-(2-Methoxy-4,5-dihydro-3H-pyrrol-3-yl)-isoindole-1,3-dione

By analogy with the method described in example 1 (step 1.1), using 2-(2-Oxo-pyrrolidin-3-yl)-isoindole-1,3-dione (prepared by analogy to the method described in (Heterocycles (1996), 42(2), 537-42, Enantiomer (2001), 6(5), 275-279, Synthesis (1991), (5), 417-20)) in place of 3-phtalimidopiperidin-2-one, the compound was obtained as a white powder.

Mp.: 139-141° C.

$^1$H NMR (DMSO-d$_6$; 200 MHz)

δ (ppm): 7.95-7.70 (m, 4H); 5.20 (dd, 1H); 3.90-3.50 (m, 5H); 2.50-2.10 (m, 2H).

8.2 2-(2-Amino-4,5-dihydro-3H-pyrrol-3-yl)-isoindole-1,3-dione hydrochloride (1:1)

By analogy with the method described in example 1 (step 1.2), using 2-(2-methoxy-4,5-dihydro-3H-pyrrol-3-yl)-isoindole-1,3-dione in place of 2-(2-methoxy-3,4,5,6-tetrahydropyridin-3-yl)-1H-isoindole-1,3(2H)-dione, the compound was obtained as a white powder.

Mp.: 121-123° C.

$^1$H NMR (DMSO-d$_6$; 200 MHz)

δ (ppm): 9.25-8.80 (br s, 3H); 7.95-7.70 (m, 4H); 5.65 (dd, 1H); 3.90-3.50 (m, 2H); 2.50-2.20 (m, 2H).

8.3 2-(4-Oxo-2-pyrimidin-4-yl-4,6,7,8-tetrahydro-pyrrolo[1,2-a]pyrimidin-8-yl)-isoindole-1,3-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate and using 2-(2-amino-4,5-dihydro-3H-pyrrol-3-yl)-isoindole-1,3-dione, the compound was obtained as a white powder.

Mp.: 180-182° C.

$^1$H NMR (DMSO-d$_6$; 200 MHz)

δ (ppm): 9.25 (s, 1H); 8.85 (d, 1H); 8.01-7.80 (m, 5H); 7.25 (s, 1H); 5.90 (dd, 1H); 4.40-3.90 (m, 2H); 2.80-2.60 (m, 2H).

8.4 8-Amino-2-pyrimidin-4-yl-7,8-dihydro-6H-pyrrolo[1,2-a]pyrimidin-4-one

By analogy with the method described in example 1 (step 1.4), using 2-(4-oxo-2-pyrimidin-4-yl-4,6,7,8-tetrahydro-pyrrolo[1,2-a]pyrimidin-8-yl)-isoindole-1,3-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 187-189° C.

$^1$H NMR (DMSO-d$_6$; 200 MHz)

δ (ppm): 9.40 (s, 1H); 9.10 (d, 1H); 8.40 (d, 1H); 7.30 (s, 1H); 4.30 (dd, 1H); 4.20-3.70 (m, 2H); 2.00-1.70 (m, 2H).

8.5 (+/−) 4-Chloro-2-methoxy-N-(4-oxo-2-pyrimidin-4-yl-4,6,7,8-tetrahydro-pyrrolo[1,2-a]pyrimidin-8-yl)-benzamide By analogy with the method described in example 1 (step 1.5), using 8-Amino-2-pyrimidin-4-yl-7,8-dihydro-6H-pyrrolo[1,2-a]pyrimidin-4-one in place of (+/−) 9-amino-2-pyridin-4-yl-6,7,8,9-tetrahydro-4H-pyrido[1,2-a]pyrimidin-4-one, the compound was obtained as a white powder.
Mp: 237-239° C.
$^1$H NMR (DMSO-d$_6$; 200 MHz)
δ (ppm): 9.35 (s, 1H); 9.02 (d, 1H); 8.96 (br d, 1H); 8.20 (d, 1H); 7.80 (d, 1H); 7.35-7.20 (m, 2H); 7.15 (dd, 1H); 5.55 (dd, 1H); 4.20-3.80 (m, 5H); 2.60-2.20 (m, 2H).

Example 9

Compound No. 2 of Table 3

(+/−) 4-Fluoro-2-methoxy-N-(4-oxo-2-pyrimidin-4-yl-4,6,7,8,9,10-hexahydropyrimido[1,2-a]azepin-10-yl)benzamide 9.1 2-(7-Methoxy-3,4,5,6-tetrahydro-2H-azepin-6-yl)-1H-isoindole-1,3(2H)-dione By analogy with the method described in example 1 (step 1.1), using α-amino-ε-caprolactam monohydrochloride (commercially available) in place of 3-phtalimidopiperidin-2-one, the compound was obtained as a yellow oil.
$^1$H NMR (CDCl3; 200 MHz)
δ (ppm): 7.92-7.66 (m, 4H); 5.10 (d, 1H); 3.90-3.70 (m, 1H); 3.50 (s, 3H); 3.40-3.30 (m, 1H); 2.70-2.50 (m, 1H); 2.1 (m, 1H); 1.90-1.20 (m, 4H).

9.2 2-(2-Iminoazepan-3-yl)-1H-isoindole-1,3(2H)-dione hydrochloride (1:1)

By analogy with the method described in example 1 (step 1.2), using 2-(7-methoxy-3,4,5,6-tetrahydro-2H-azepin-6-yl)-1H-isoindole-1,3(2H)-dione in place of 2-(2-methoxy-3,4,5,6-tetrahydropyridin-3-yl)-1H-isoindole-1,3(2H)-dione, the compound was obtained as a white powder.
Mp.: 120-122° C.
$^1$H NMR (CDCl3; 200 MHz)
δ (ppm): 9.40 (br s, 1H); 8.70 (br s, 1H); 8.20-7.60 (m, 4H); 5.28 (br t, 1H); 3.90-3.40 (m, 3H); 2.30-1.30 (m, 5H).

9.3 (+/−) 2-(4-Oxo-2-pyrimidin-4-yl-4,6,7,8,9,10-hexahydropyrimido[1,2-a]azepin-10-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate and using 2-(2-iminoazepan-3-yl)-1H-isoindole-1,3(2H)-dione hydrochloride (1:1), the compound was obtained as a white powder.
Mp.: 250-252° C.
$^1$H NMR (DMSO-d$_6$; 200 MHz)
δ (ppm): 9.30 (s, 1H); 8.60 (d, 1H); 8.00 (m, 3H); 7.40 (m, 1H); 7.20 (m, 2H); 4.70 (d, 2H); 3.50 (m, 2H); 2.00-1.50 (m, 4H); 1.3 (m, 1H).

9.4 (+/−) 10-Amino-2-pyrimidin-4-yl-7,8,9,10-tetrahydropyrimido[1,2-a]azepin-4(6H)-one By analogy with the method described in example 1 (step 1.4), using (+/−) 2-(4-oxo-2-pyrimidin-4-yl-4,6,7,8,9,10-hexahydropyrimido[1,2-a]azepin-10-yl)-1H-isoindole-1,3(2H)-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.
Mp.: 157-159° C.
$^1$H NMR (DMSO-d$_6$; 200 MHz)
δ (ppm): 9.30 (s, 1H); 9.00 (d, 1H); 8.40 (d, 1H); 7.20 (s, 1H); 5.00-4.80 (m, 1H); 4.25 (d, 1H); 3.80-3.60 (dd, 1H); 2.00-1.20 (m, 6H).

9.5 (+/−) 4-Fluoro-2-methoxy-N-(4-oxo-2-pyrimidin-4-yl-4,6,7,8,9,10-hexahydropyrimido[1,2-a]azepin-10-yl)benzamide By analogy with the method described in example 1 (step 1.5), using (+/−) 10-amino-2-pyrimidin-4-yl-7,8,9,10-tetrahydropyrimido[1,2-a]azepin-4(6H)-one in place of (+/−) 9-amino-2-pyridin-4-yl-6,7,8,9-tetrahydro-4H-pyrido[1,2-a]pyrimidin-4-one, the compound was obtained as a white powder.
Mp: 324-326° C.
$^1$H NMR (DMSO-d$_6$; 200 MHz)
δ (ppm): 9.32 (m, 2H); 9.05 (d, 2H); 8.25 (d, 1H); 8.00 (t, 1H); 7.30 (s, 1H); 7.15 (d, 1H); 6.90 (dd, 1H); 5.40 (d, 1H); 5.00 (dd, 1H); 4.00 (s, 3H); 2.20-1.80 (m, 5H); 1.30 (m, 1H).

Example 10

Compound No. 15 of Table 3

(+) 4-Fluoro-2-methoxy-N-(4-oxo-2-pyrimidin-4-yl-4,6,7,8,9,10-hexahydropyrimido[1,2-a]azepin-10-yl)benzamide 143 mg (0.35 mmol) of (+/−) 4-fluoro-2-methoxy-N-(4-oxo-2-pyrimidin-4-yl-4,6,7,8,9,10-hexahydropyrimido[1,2-a]azepin-10-yl)benzamide (compound N° 2, table 3) was separated by chiral preparative HPLC (CHIRALCEL OD-CSP 50×250) eluting with ethanol to give to give 0.033 g of pure product obtained in the form of free base. $t_R$: 9.0 min.
Mp: 241.7° C. $[α]_D^{20}$=+4.6° (c=0.167, DMSO).
δ (ppm): 9.32 (m, 2H); 9.05 (d, 2H); 8.25 (d, 1H); 8.00 (t, 1H); 7.30 (s, 1H); 7.15 (d, 1H); 6.90 (dd, 1H); 5.40 (d, 1H); 5.00 (dd, 1H); 4.00 (s, 3H); 2.20-1.80 (m, 5H); 1.30 (m, 1H).

Example 11

Compound No. 16 of Table 3

(−) 4-Fluoro-2-methoxy-N-(4-oxo-2-pyrimidin-4-yl-4,6,7,8,9,10-hexahydropyrimido[1,2-a]azepin-10-yl)benzamide 143 mg (0.35 mmol) of (+/−) 4-fluoro-2-methoxy-N-(4-oxo-2-pyrimidin-4-yl-4,6,7,8,9,10-hexahydropyrimido[1,2-a]azepin-10-yl)benzamide (compound N° 2, table 3) was separated by chiral preparative HPLC (CHIRALCEL OD-CSP 50×250) eluting with ethanol to give 0.035 g of pure product obtained in the form of free base. $t_R$: 7.1 min.
Mp: 232.7-233.2° C. $[α]_D^{20}$=−5.3° (c=0.135, DMSO).
δ (ppm): 9.32 (m, 2H); 9.05 (d, 2H); 8.25 (d, 1H); 8.00 (t, 1H); 7.30 (s, 1H); 7.15 (d, 1H); 6.90 (dd, 1H); 5.40 (d, 1H); 5.00 (dd, 1H); 4.00 (s, 3H); 2.20-1.80 (m, 5H); 1.30 (m, 1H).

Example 12

Compound No. 47 of Table 1

(+/−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide

12.1 2-(2-Methoxy-3-methyl-3,4,5,6-tetrahydropyridin-3-yl)-1H-isoindole-1,3(2H)-dione By analogy with the method described in example 1 (step 1.1), using 2-(3-methyl-2-oxopiperidin-3-yl)-1H-isoindole-1,3(2H)-dione (prepared by analogy to the method described in Liebigs Annalen der Chemie (1987), (7), 647-8. Archiv der Pharmazie (Weinheim, Germany) (1989), 322(8), 499-505, (Heterocycles (1996), 42(2), 537-42, Enantiomer (2001), 6(5), 275-279, Synthesis (1991), (5), 417-20)) in place of 3-phtalimidopiperidin-2-one, the compound was obtained as a yellow oil.

$^1$H NMR (DMSO-d$_6$; 200 MHz)

δ (ppm): 7.80 (m, 4H); 3.40 (m, 4H); 2.30-2.10 (m, 1H); 1.90-1.70 (m, 5H); 1.65-1.40 (m, 2H).

12.2 2-(2-Amino-3-methyl-3,4,5,6-tetrahydropyridin-3-yl)-1H-isoindole-1,3(2H)-dione hydrochloride (1:1)

By analogy with the method described in example 1 (step 1.2), using 2-(2-methoxy-3-methyl-3,4,5,6-tetrahydropyridin-3-yl)-1H-isoindole-1,3(2H)-dione in place of 2-(2-methoxy-3,4,5,6-tetrahydropyridin-3-yl)-1H-isoindole-1,3(2H)-dione, the compound was obtained as a white powder.

Mp.: 165-167° C.

$^1$H NMR (DMSO-d$_6$; 200 MHz)

δ (ppm): 7.70-7.10 (m, 4H); 3.20-3.00 (m, 2H); 2.40-2.20 (m, 1H); 1.80-1.60 (m, 3H); 1.20 (s, 3H).

12.3 (+/−) 2-(1-Methyl-5-oxo-7-pyrimidin-4-yl-1,2,3,4,4a,5-hexahydronaphthalen-1-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate and using 2-(2-amino-3-methyl-3,4,5,6-tetrahydropyridin-3-yl)-1H-isoindole-1,3(2H)-dione hydrochloride (1:1) the compound was obtained as a white powder.

Mp.: 184-186° C.

$^1$H NMR (DMSO-d$_6$; 200 MHz)

δ (ppm): 9.25 (s, 1H); 8.80 (d, 1H); 8.00 (d, 2H); 7.80 (m, 4H); 7.20 (s, 1H); 4.30-4.10 (dt, 1H); 3.80-3.60 (m, 1H); 2.50 (m, 1H); 2.15 (s, 3H); 2.10-1.80 (m, 2H).

12.4 (+/−) 5-Amino-5-methyl-3-pyrimidin-4-yl-6,7,8,8a-tetrahydronaphthalen-1(5H)-one By analogy with the method described in example 1 (step 1.4), using (+/−) 2-(1-methyl-5-oxo-7-pyrimidin-4-yl-1,2,3,4,4a,5-hexahydronaphthalen-1-yl)-1H-isoindole-1,3(2H)-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 138-140° C.

$^1$H NMR (DMSO-d$_6$; 200 MHz)

δ (ppm): 9.25 (s, 1H); 9.00 (d, 1H); 8.40 (d, 2H); 7.15 (s, 1H); 4.00-3.70 (m, 2H); 2.30 (br s, 2H); 2.10-1.70 (m, 3H); 1.45 (s, 3H).

12.5 (+/−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide By analogy with the method described in example 1 (step 1.5), using (+/−) 5-amino-5-methyl-3-pyrimidin-4-yl-6,7,8,8a-tetrahydronaphthalen-1(5H)-one in place of (+/−) 9-amino-2-pyridin-4-yl-6,7,8,9-tetrahydro-4H-pyrido[1,2-a]pyrimidin-4-one, the compound was obtained as a white powder.

Mp: 192-194° C.

$^1$H NMR (DMSO-d$_6$; 200 MHz)

δ (ppm): 9.30 (s, 1H); 9.00 (d, 1H); 8.80 (br s, 1H); 8.20 (d, 1H); 7.50 (d, 1H); 7.20 (d, 1H); 7.15 (s, 1H); 7.05 (dd, 1H); 4.40-4.20 (br d, 1H); 3.90 (s, 3H); 3.70-3.50 (m, 1H); 2.50 (m, 1H); 2.20-1.90 (m, 3H); 1.70 (s, 3H).

Example 13

Compound No. 48 of Table 1

(+) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide 480 mg (1.13 mmol) of (+/−) 4-chloro-2-methoxy-N-(9-methyl-4-oxo-2-pyrimidin-4-yl-6,7,8,9-tetrahydro-4H-pyrido[1,2-a]pyrimidin-9-yl)benzamide (compound No. 47 of table 1) was separated by chiral preparative HPLC (CHIRALCEL OD-CSP 20 µm 250×50 mm) eluting with a mixture of isopropanol/heptane to give 181 mg of pure product obtained in the form of free base.

Mp: 181.7° C. $[\alpha]_D^{20}$=+132.4° (c=0.2618, DMSO).

$^1$H NMR (DMSO-d$_6$; 200 MHz)

δ (ppm): 9.30 (s, 1H); 9.00 (d, 1H); 8.80 (br s, 1H); 8.20 (d, 1H); 7.50 (d, 1H); 7.20 (d, 1H); 7.15 (s, 1H); 7.05 (dd, 1H); 4.40-4.20 (br d, 1H); 3.90 (s, 3H); 3.70-3.50 (m, 1H); 2.50 (m, 1H); 2.20-1.90 (m, 3H); 1.70 (s, 3H).

Example 14

Compound No. 49 of Table 1

(−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide 480 mg (1.13 mmol) of (+/−) 4-chloro-2-methoxy-N-(9-methyl-4-oxo-2-pyrimidin-4-yl-6,7,8,9-tetrahydro-4H-pyrido[1,2-a]pyrimidin-9-yl)benzamide (compound No. 47 of table 1) was separated by chiral preparative HPLC (CHIRALCEL OD-CSP 20 µm 250×50 mm) eluting with a mixture of isopropanol/heptane to give 202 mg of pure product obtained in the form of free base.

Mp: 182.7° C. $[\alpha]_D^{20}$=−126.1° (c=0.4055, DMSO).

$^1$H NMR (DMSO-d$_6$; 200 MHz)

δ (ppm): 9.30 (s, 1H); 9.00 (d, 1H); 8.80 (br s, 1H); 8.20 (d, 1H); 7.50 (d, 1H); 7.20 (d, 1H); 7.15 (s, 1H); 7.05 (dd, 1H); 4.40-4.20 (br d, 1H); 3.90 (s, 3H); 3.70-3.50 (m, 1H); 2.50 (m, 1H); 2.20-1.90 (m, 3H); 1.70 (s, 3H).

Example 15

Compound No. 5 of Table 2

(+/−) 4-Chloro-2-methoxy-N-(4-oxo-2-pyridin-4-yl-4,6,7,8-tetrahydro-pyrrolo[1,2-a]pyrimidin-8-yl)-benzamide 15.1 (+/−) 2-(4-Oxo-2-pyridin-4-yl-4,6,7,8-tetrahydro-pyrrolo[1,2-a]pyrimidin-8-yl)-isoindole-1,3-dione By analogy with the method described in example 1 (step 1.3), using ethyl 3-(4-pyridinyl)-3-oxopropionate (prepared by analogy to the method described in patent DE 2705582) and using 2-(2-amino-4,5-dihydro-3H-pyrrol-3-yl)-isoindole-1,3-dione, the compound was obtained as a white powder.
Mp.: 224-226° C.
$^1$H NMR (DMSO-d$_6$; 200 MHz)
δ (ppm): 8.60 (d, 2H); 8.00-7.70 (m, 6H); 7.05 (s, 1H); 5.90 (t, 1H); 4.40-4.20 (m, 1H); 3.80-4.10 (m, 1H); 2.70-2.40 (m, 2H).

15.2 (+/−) 8-Amino-2-pyridin-4-yl-7,8-dihydro-6H-pyrrolo[1,2-a]pyrimidin-4-one

By analogy with the method described in example 1 (step 1.4), using 2-(4-oxo-2-pyridin-4-yl-4,6,7,8-tetrahydro-pyrrolo[1,2-a]pyrimidin-8-yl)-isoindole-1,3-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.
Mp.: 187-189° C.
$^1$H NMR (DMSO-d$_6$; 200 MHz)
δ (ppm): 8.70 (d, 2H); 8.00 (d, 2H); 7.00 (s, 1H); 4.40-4.20 (m, 1H); 3.90-4.10 (m, 1H); 3.90-3.60 (m, 1H); 2.60-2.30 (m, 1H); 1.70-2.00 (m, 1H).

15.3 (+/−) 4-Chloro-2-methoxy-N-(4-oxo-2-pyridin-4-yl-4,6,7,8-tetrahydro-pyrrolo[1,2-a]pyrimidin-8-yl)-benzamide By analogy with the method described in example 1 (step 1.5), using 8-Amino-2-pyridin-4-yl-7,8-dihydro-6H-pyrrolo[1,2-a]pyrimidin-4-one in place of (+/−) 9-amino-2-pyridin-4-yl-6,7,8,9-tetrahydro-4H-pyrido[1,2-a]pyrimidin-4-one, the compound was obtained as a white powder.
Mp: 303-305° C.
RMN $^1$H (DMSO-d$^6$; 200 MHz)
δ (ppm): 8.90 (d, 1H); 8.70 (d, 2H); 8.00 (d, 2H); 7.80 (d, 1H); 7.25 (s, 1H); 7.15-6.90 (m, 2H); 5.50 (m, 1H); 4.20 (m, 1H); 3.95-3.70 (m, 4H); 2.60 (m, 1H); 2.20 (m, 1H).

Example 16

Compound No. 19 of Table 3

(+/−) 4-Fluoro-2-methoxy-N-(4-oxo-2-pyridin-4-yl-4,6,7,8,9,10-hexahydropyrimido[1,2-a]azepin-10-yl)benzamide 16.1 (+/−) 2-(4-Oxo-2-pyridin-4-yl-4,6,7,8,9,10-hexahydropyrimido[1,2-a]azepin-10-yl)-1H-isoindole-1,3(2H)-dione By analogy with the method described in example 1 (step 1.3), using ethyl 3-(pyridin-4-yl)-3-oxopropionate and using 2-(2-iminoazepan-3-yl)-1H-isoindole-1,3(2H)-dione hydrochloride (1:1), the compound was obtained as a white powder.
Mp.: 250-252° C.
$^1$H NMR (DMSO-d$_6$; 200 MHz)
δ (ppm): 8.40 (d, 2H); 8.00-7.80 (m, 4H); 7.50 (d, 2H); 7.08 (s, 1H); 5.65 (brd, 1H); 5.10 (brd, 1H); 3.75 (m, 1H); 2.80-2.3 (m, 1H); 2.10-1.70 (m, 4H); 1.4 (m, 1H).

16.2 (+/−) 10-Amino-2-pyridin-4-yl-7,8,9,10-tetrahydropyrimido[1,2-a]azepin-4(6H)-one By analogy with the method described in example 1 (step 1.4), using (+/−) 2-(4-oxo-2-pyridin-4-yl-4,6,7,8,9,10-hexahydropyrimido[1,2-a]azepin-10-yl)-1H-isoindole-1,3 (2H)-dione in place of (+/−) 2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.
Mp.: 181-183° C.
$^1$H NMR (DMSO-d$_6$; 200 MHz)
δ (ppm): 8.70 (d, 2H); 8.10 (d, 2H); 7.50 (d, 2H); 7.10 (s, 1H); 4.90 (brd, 1H); 4.25 (d, 1H); 3.75 (ddd, 1H); 2.00-1.70 (m, 2H); 1.60-1.20 (m, 4H).

16.3 (+/−) 4-Fluoro-2-methoxy-N-(4-oxo-2-pyridin-4-yl-4,6,7,8,9,10-hexahydropyrimido[1,2-a]azepin-10-yl)benzamide By analogy with the method described in example 1 (step 1.5), using (+/−) 10-amino-2-pyridin-4-yl-7,8,9,10-tetrahydropyrimido[1,2-a]azepin-4(6H)-one in place of (+/−) 9-amino-2-pyridin-4-yl-6,7,8,9-tetrahydro-4H-pyrido[1,2-a]pyrimidin-4-one, the compound was obtained as a white powder.
Mp: 218-220° C.
$^1$H NMR (DMSO-d$_6$; 200 MHz)
δ (ppm): 9.40 (d, 1H); 8.80 (d, 2H); 8.00 (m, 3H); 7.20-6.85 (m, 3H); 5.40 (m, 1H); 5.00 (m, 1H); 3.95 (s, 3H); 3.65 (m, 1H); 2.25-1.15 (m, 6H).

Example 17

Compound No. 51 of Table 1

(+) 4-Fluoro-2-methoxy-N-(4-oxo-2-pyrimidin-4-yl-6,7,8,9-tetrahydro-4H-pyrido[1,2-a]pyrimidin-9-yl)benzamide 0.556 g (1.42 mmol) of (+/−) 4-fluoro-2-methoxy-N-(4-oxo-2-pyrimidin-4-yl-6,7,8,9-tetrahydro-4H-pyrido[1,2-a]pyrimidin-9-yl)benzamide was separated by chiral preparative HPLC (Daicel CHIRALCEL OD-H 20 μm 50×220 mm) eluting with ethanol to give 0.162 g of pure product obtained in the form of free base.
Mp: >240° C. (dec.). $[α]_D^{20}$=+54.7° (c=0.321, DMSO).
$^1$H NMR (DMSO-d$_6$; 200 MHz)
δ (ppm): 9.40 (s, 1H); 9.05 (d, 1H); 8.90 (d, 1H); 8.20 (d, 1H); 7.90 (dd, 1H); 7.25 (s, 1H); 7.10 (dd, 1H); 6.90 (ddd, 1H); 5.15 (m, 1H); 4.00 (m, 2H); 3.90 (s, 3H); 2.30 (m, 1H); 2.10 (m, 2H); 1.80 (m, 1H).

Example 18

Compound No. 52 of Table 1

(−) 4-Fluoro-2-methoxy-N-(4-oxo-2-pyrimidin-4-yl-6,7,8,9-tetrahydro-4H-pyrido[1,2-a]pyrimidin-9-yl)benzamide 0.556 g (1.42 mmol) of (+/−) 4-fluoro-2-methoxy-N-(4-oxo-2-pyrimidin-4-yl-6,7,8,9-tetrahydro-4H-pyrido[1,2-a]pyrimidin-9-yl)benzamide was separated by chiral preparative HPLC (Daicel CHIRALCEL OD-H 20 μm 50×220 mm) eluting with ethanol to give 0.174 g of pure product obtained in the form of free base.
Mp: >240° C. (dec.). $[α]_D^{20}$=−53.9° (c=0.231, DMSO).

¹H NMR (DMSO-d₆; 200 MHz)
δ (ppm): 9.40 (s, 1H); 9.05 (d, 1H); 8.90 (d, 1H); 8.20 (d, 1H); 7.90 (dd, 1H); 7.25 (s, 1H); 7.10 (dd, 1H); 6.90 (ddd, 1H); 5.15 (m, 1H); 4.00 (m, 2H); 3.90 (s, 3H); 2.30 (m, 1H); 2.10 (m, 2H); 1.80 (m, 1H).

Example 19

Compound No. 25 of Table 3

(+) 4-Chloro-2-methoxy-N-(4-oxo-2-pyrimidin-4-yl-4,6,7,8,9,10-hexahydropyrimido[1,2-a]azepin-10-yl) benzamide 19.1 (−) 10-amino-2-pyrimidin-4-yl-7,8,9,10-tetrahydropyrimido[1,2-a]azepin-4(6H)-one 20 g (77.73 mmol) of 9.4 (+/−) 10-Amino-2-pyrimidin-4-yl-7,8,9,10-tetrahydropyrimido[1,2-a]azepin-4(6H)-one (compound 9.4 of example 9) was separated by chiral preparative HPLC (Daicel CHIRALPACK AD 20 μm 50×220 mm) eluting with ethanol to give 9.05 g of pure product obtained in the form of free base.
Mp.: 117.8° C. $[\alpha]_D^{20}$=−59.76° (c=0.619, DMSO).
¹H NMR (DMSO-d₆; 200 MHz)
δ (ppm): 9.3 (s, 1H); 9.0 (d, 1H); 8.4 (d, 1H); 7.2 (s, 1H); 5.0-4.8 (m, 1H); 4.25 (d, 1H); 3.8-3.6 (dd, 1H); 2.0-1.2 (m, 6H).

19.2 (+) 4-Chloro-2-methoxy-N-(4-oxo-2-pyrimidin-4-yl-4,6,7,8,9,10-hexahydropyrimido[1,2-a]azepin-10-yl)benzamide By analogy with the method described in example 1 (step 1.5), using (−) 10-amino-2-pyrimidin-4-yl-7,8,9,10-tetrahydropyrimido[1,2-a]azepin-4(6H)-one in place of (+/−) 9-amino-2-pyridin-4-yl-6,7,8,9-tetrahydro-4H-pyrido[1,2-a]pyrimidin-4-one, the compound was obtained as a white powder.
Mp.: 210-212° C. $[\alpha]_D^{20}$=+8.99° (c=0.403, DMSO).
¹H NMR (DMSO-d₆; 200 MHz)
δ (ppm): 9.47 (bd, 1H); 9.40 (s, 1H); 8.90 (d, 1H); 8.20 (m, 2H); 7.55 (s, 1H); 7.10 (m, 2H); 7.15 (d, 1H); 5.50 (m, 2H); 4.00 (s, 3H); 3.55 (m, 1H); 2.50 (bd, 1H); 2.20 (m, 2H); 1.80-1.40 (m, 3H).

Example 20

Compound No. 26 of Table 3

(−) 4-Chloro-2-methoxy-N-(4-oxo-2-pyrimidin-4-yl-4,6,7,8,9,10-hexahydropyrimido[1,2-a]azepin-10-yl) benzamide 20.1 (+) 10-amino-2-pyrimidin-4-yl-7,8,9,10-tetrahydropyrimido[1,2-a]azepin-4(6H)-one 20 g (77.73 mmol) of (+/−) 10-amino-2-pyrimidin-4-yl-7,8,9,10-tetrahydropyrimido[1,2-a]azepin-4(6H)-one was separated by chiral preparative HPLC (Daicel CHIRALPACK AD 20 μm 50×220 mm) eluting with ethanol to give 9.17 g of pure product obtained in the form of free base.
Mp.: 118° C. $[\alpha]_D^{20}$=+59.97° (c=0.691, DMSO).
¹H NMR (DMSO-d₆; 200 MHz)
δ (ppm): 9.3 (s, 1H); 9.0 (d, 1H); 8.4 (d, 1H); 7.2 (s, 1H); 5.0-4.8 (m, 1H); 4.25 (d, 1H); 3.8-3.6 (dd, 1H); 2.0-1.2 (m, 6H).

20.2 (−) 4-Chloro-2-methoxy-N-(4-oxo-2-pyrimidin-4-yl-4,6,7,8,9,10-hexahydropyrimido[1,2-a]azepin-10-yl)benzamide By analogy with the method described in example 1 (step 1.5), using (+) 10-amino-2-pyrimidin-4-yl-7,8,9,10-tetrahydropyrimido[1,2-a]azepin-4(6H)-one in place of (+/−) 9-amino-2-pyridin-4-yl-6,7,8,9-tetrahydro-4H-pyrido[1,2-a]pyrimidin-4-one, the compound was obtained as a white powder.
Mp.: 212-214° C. $[\alpha]_D^{20}$=−8.8° (c=0.510, DMSO).
¹H NMR (DMSO-d₆; 200 MHz)
δ (ppm): 9.47 (bd, 1H); 9.40 (s, 1H); 8.90 (d, 1H); 8.20 (m, 2H); 7.55 (s, 1H); 7.10 (m, 2H); 7.15 (d, 1H); 5.50 (m, 2H); 4.00 (s, 3H); 3.55 (m, 1H); 2.50 (bd, 1H); 2.20 (m, 2H); 1.80-1.40 (m, 3H).

A list of chemical structures and physical data for compounds of the aforementioned formula (I), illustrating the present invention, is given in table 1. The compounds have been prepared according to the methods of the examples. In the table, m and o represent 1, Ph represents a phenyl group, Me represent a methyl group, (Rot.) indicates the levorotatory or dextrorotatory properties of the enantiomeric compound.

TABLE 1

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 1 | (+/−) | Ph | bond | pyrimidinyl | H | H | H | H | O | H | 0 | 208-210 | Free base |

TABLE 1-continued
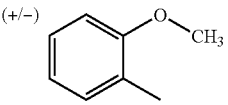
(I)
| No. | Rot | R2 | Z | R1 | R4 | R5 | R6 | R7 | Y | R3 | n | Mp °C. | salt |
|---|---|---|---|---|---|---|---|---|---|---|---|---|---|
| 2 | (+/−) | 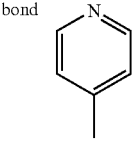 | bond | 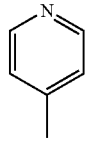 | H | H | H | H | O | H | 0 | 155-157 | Free base |
| 3 | (+/−) | Ph | bond | 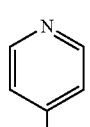 | H | H | H | H | O | H | 1 | 200-202 | Free base |
| 4 | (+/−) | Ph | O | 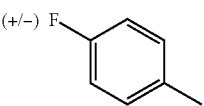 | H | H | H | H | O | H | 0 | 193-195 | Free base |
| 5 | (+/−) | 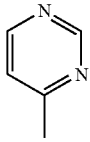 | NH | 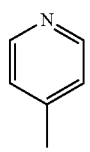 | H | H | H | H | O | H | 0 | 251-253 | Free base |
| 6 | (+/−) | Ph | NH | 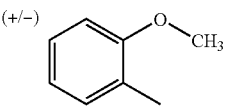 | H | H | H | H | O | H | 0 | 254-256 | Free base |
| 7 | (+/−) | 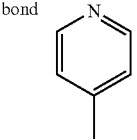 | bond | 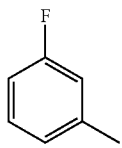 | H | H | H | H | H, H | H | 0 | 230-232 | Hydrochloride (2:1) |
| 8 | (+/−) | 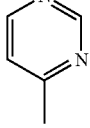 | bond | 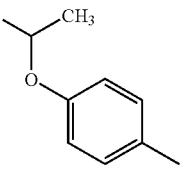 | H | H | H | H | O | H | 0 | 204-206 | Free base |
| 9 | (+/−) | 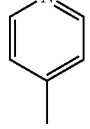 | bond | 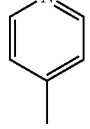 | H | H | H | H | O | H | 0 | 229-231 | Free base |

TABLE 1-continued
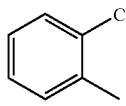
(I)
| No. | Rot | R2 | Z | R1 | R4 | R5 | R6 | R7 | Y | R3 | n | Mp °C. | salt |
|---|---|---|---|---|---|---|---|---|---|---|---|---|---|
| 10 | (+/−) | 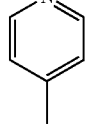 | bond | 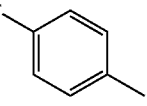 | H | H | H | H | O | H | 0 | 205-207 | Free base |
| 11 | (+/−) | 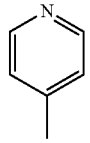 | bond | 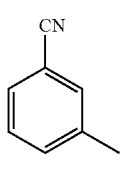 | H | H | H | H | O | H | 0 | 194-196 | Free base |
| 12 | (+/−) | 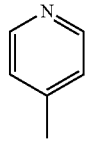 | bond | 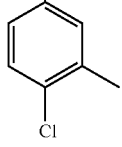 | H | H | H | H | O | H | 0 | 219-221 | Free base |
| 13 | (+/−) | 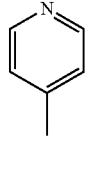 | bond | 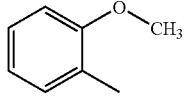 | H | H | H | H | O | H | 0 | 198-200 | Free base |
| 14 | (+/−) | 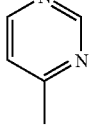 | bond | 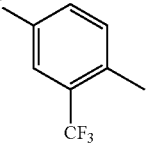 | H | H | H | H | O | H | 0 | 249-251 | Free base |
| 15 | (+/−) | 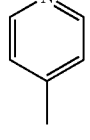 | bond | 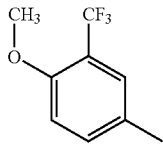 | H | H | H | H | O | H | 0 | 187-189 | Free base |
| 16 | (+/−) | 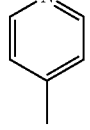 | bond | 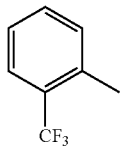 | H | H | H | H | O | H | 0 | 200-202 | Free base |
| 17 | (+/−) | 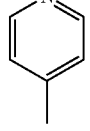 | bond | | H | H | H | H | O | H | 0 | 204-206 | Free base |

TABLE 1-continued

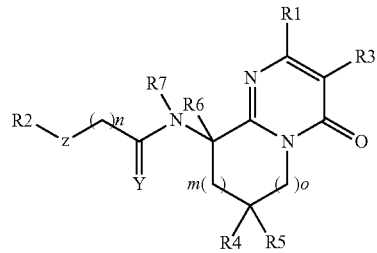

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 18 | (+/−) | 2-F, 4-NO2, 5-Cl phenyl | bond | 4-pyridyl | H | H | H | H | O | H | 0 | 187-189 | Free base |
| 19 | (+/−) | 2-naphthyl | bond | 4-pyridyl | H | H | H | H | O | H | 0 | 262-264 | Free base |
| 20 | (+/−) | 3-Cl phenyl | bond | 4-pyridyl | H | H | H | H | O | H | 0 | 213-215 | Free base |
| 21 | (+/−) | 2,6-dimethoxyphenyl | bond | 4-pyrimidinyl | H | H | H | H | O | H | 0 | 200-202 | Free base |
| 22 | (+/−) | 3-methoxyphenyl | bond | 4-pyrimidinyl | H | H | H | H | O | H | 0 | 197-199 | Free base |
| 23 | (+/−) | 2-methoxy-6-F phenyl | bond | 4-pyrimidinyl | H | H | H | H | O | H | 0 | 181-183 | Free base |
| 24 | (+/−) | 4-F, 2-methoxyphenyl | bond | 4-pyridyl | H | H | H | H | O | H | 0 | 234-236 | Free base |

TABLE 1-continued
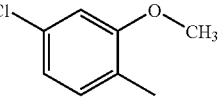
| No. | Rot | R2 | Z | R1 | R4 | R5 | R6 | R7 | Y | R3 | n | Mp ° C. | salt |
|---|---|---|---|---|---|---|---|---|---|---|---|---|---|
| 25 | (+/−) | 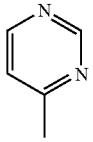 | bond | 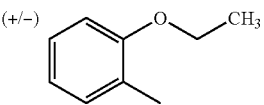 | H | H | H | H | O | H | 0 | 218-220 | Free base |
| 26 | (+/−) | 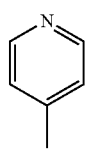 | bond | 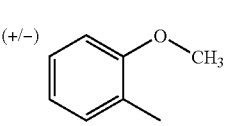 | H | H | H | H | O | H | 0 | 190-192 | Free base |
| 27 | (+/−) | 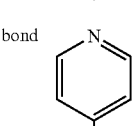 | bond | 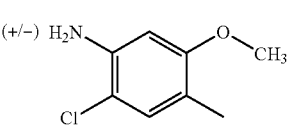 | H | H | H | H | O | Br | 0 | 256-257.3 | Free base |
| 28 | (+/−) | 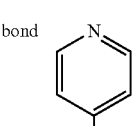 | bond | 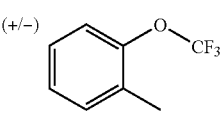 | H | H | H | H | O | H | 0 | 249-251 | Free base |
| 29 | (+/−) | 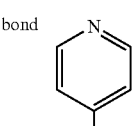 | bond | 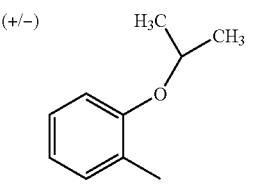 | H | H | H | H | O | H | 0 | 172-174 | Free base |
| 30 | (+/−) | 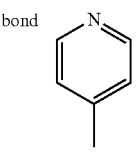 | bond | 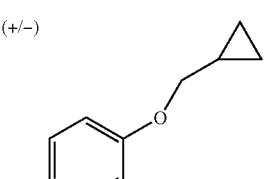 | H | H | H | H | O | H | 0 | 170-172 | Free base |
| 31 | (+/−) | 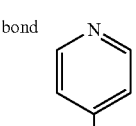 | bond | 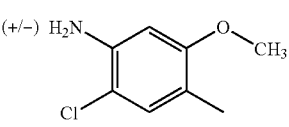 | H | H | H | H | O | H | 0 | 202-204 | Free base |
| 32 | (+/−) | 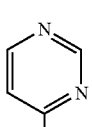 | bond | | H | H | H | H | O | H | 0 | 228-230 | Free base |

TABLE 1-continued (I)

| No. | Rot | R2 | Z | R1 | R4 | R5 | R6 | R7 | Y | R3 | n | Mp ° C. | salt |
|-----|-----|----|----|----|----|----|----|----|---|----|---|---------|------|
| 33 | (+/−) | 5-fluoro-2-methyl-3-methoxyphenyl | bond | pyrimidin-4-yl | H | H | H | H | O | H | 0 | 221-223 | Free base |
| 34 | (+/−) | 2-methyl-(cyclopropylmethoxy)phenyl | bond | pyrimidin-4-yl | H | H | H | H | O | H | 0 | 169-171 | Free base |
| 35 | (+/−) | naphthalen-2-yl-methyl | bond | pyrimidin-4-yl | H | H | H | H | O | H | 0 | 223-225 | Free base |
| 36 | (+/−) | 3-chlorophenyl | bond | pyrimidin-4-yl | H | H | H | H | O | H | 0 | 202-204 | Free base |
| 37 | (+/−) | 4-chloro-2-methyl-3-methoxyphenyl | bond | pyrimidin-4-yl | H | H | H | H | O | H | 0 | 229-231 | Free base |
| 38 | (+/−) | 5-amino-2-methyl-3-methoxyphenyl | Bond | pyrimidin-4-yl | H | H | H | H | O | H | 0 | 246-248 | Free base |
| 39 | (+/−) | 5-trifluoromethyl-2-methyl-3-methoxyphenyl | Bond | pyrimidin-4-yl | H | H | H | H | O | H | 0 | 206-208 | Free base |

TABLE 1-continued

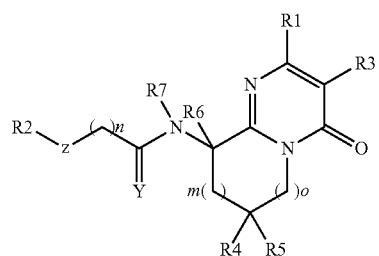
(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 40 | (+/−) | 4-methoxy-3-methyl-phenyl ethylsulfonyl | Bond | 4-pyrimidinyl | H | H | H | H | O | H | 0 | 227-229 | Free base |
| 41 | (+/−) | 2,3-dimethoxy-methylphenyl | Bond | 4-pyrimidinyl | H | H | H | H | O | H | 0 | 202-204 | Free base |
| 42 | (−) | 4-chloro-2-methoxy-methylphenyl | Bond | 4-pyrimidinyl | H | H | H | H | O | H | 0 | 174-176 | Free base |
| 43 | (+) | 4-chloro-2-methoxy-methylphenyl | Bond | 4-pyrimidinyl | H | H | H | H | O | H | 0 | 175-177 | Free base |
| 44 | (+/−) | 4-bromo-2-methyl-methoxy-phenyl | Bond | 4-pyrimidinyl | H | H | H | H | O | H | 0 | 216-218 | Free base |
| 45 | (+/−) | 2-methylphenyl acetate | bond | 4-pyrimidinyl | H | H | H | H | O | H | 0 | 322-324 | Free base |
| 46 | (+/−) | 2-methylphenol | bond | 4-pyrimidinyl | H | H | H | H | O | H | 0 | 214-216 | Free base |

TABLE 1-continued (I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 47 | (+/−) | 5-Cl, 2-OCH3, methylphenyl | bond | pyrimidin-4-yl | H | H | CH3 | H | O | H | 0 | 192-194 | Free base |
| 48 | (+) | 5-Cl, 2-OCH3, methylphenyl | bond | pyrimidin-4-yl | H | H | CH3 | H | O | H | 0 | 181.7 | Free base |
| 49 | (−) | 5-Cl, 2-OCH3, methylphenyl | bond | pyrimidin-4-yl | H | H | CH3 | H | O | H | 0 | 182.7 | Free base |
| 50 | (+/−) | 5-Cl, 2-OCH3, methylphenyl | bond | pyrimidin-4-yl | H | H | H | Me | O | H | 0 | 167-169 | Free base |
| 51 | (+) | 5-F, 2-OCH3, methylphenyl | bond | pyrimidin-4-yl | H | H | H | H | O | H | 0 | >240 (dec.) | Free base |
| 52 | (−) | 5-F, 2-OCH3, methylphenyl | bond | pyrimidin-4-yl | H | H | H | H | O | H | 0 | >240 (dec.) | Free base |
| 53 | (+/−) | 4-Cl, 2-OCH3, methylphenyl | bond | pyrimidin-4-yl | H | H | Me | H | O | H | 0 | 188-190 | Free base |
| 54 | (+/−) | 5-F, 2-OCH3, methylphenyl | bond | pyrimidin-4-yl | H | H | Me | H | O | H | 0 | 191-193 | Free base |

TABLE 1-continued

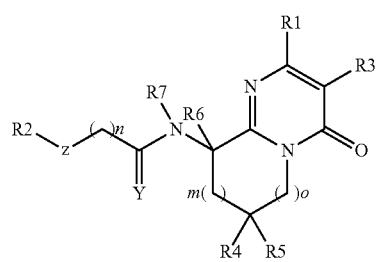

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 55 | (+/−) | H2N-C6H3(Cl)(OCH3)(CH3) | bond | pyrimidinyl | H | H | Me | H | O | H | 0 | 256-258 | Free base |
| 56 | (+/−) | CF3-C6H3(OCH3)(CH3) | bond | pyrimidinyl | H | H | ME | H | O | H | 0 | 181-183 | Free base |
| 57 | (+/−) | C6H3(OCH3)(CH3)(F) | bond | pyrimidinyl | H | H | Me | H | O | H | 0 | 210-212 | Free base |
| 58 | (+/−) | C6H4(OCF3)(CH3) | bond | pyrimidinyl | H | H | Me | H | O | H | 0 | 180-182 | Free base |
| 59 | (+/−) | C6H2(Br)(CH3)(OCH3) | bond | pyrimidinyl | H | H | Me | H | O | H | 0 | 206-208 | Free base |
| 60 | (+/−) | (CH3)2N-C6H3(OCH3)(CH3) | bond | pyrimidinyl | H | H | Me | H | O | H | 0 | 275-277 | Free base |
| 61 | (+/−) | CH3O-C6H3(OCH3)(CH3) | bond | pyrimidinyl | H | H | Me | H | O | H | 0 | 198-200 | Free base |

A list of chemical structures and physical data for compounds of the aforementioned formula (I), illustrating the present invention, is given in table 2. The compounds have been prepared according to the methods of the examples. In the table, m represents 0 and o represents 1, (Rot.) indicates the levorotatory or dextrorotatory properties of the enantiomeric compound.

TABLE 2

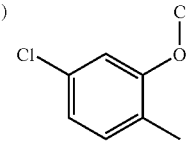

| No. | Rot | R2 | Z | R1 | R4 | R5 | R6 | R7 | Y | R3 | n | Mp °C. | salt |
|---|---|---|---|---|---|---|---|---|---|---|---|---|---|
| 1 | (+/−) | 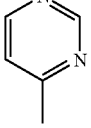 | bond | 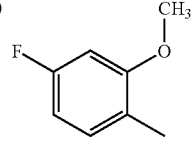 | H | H | H | H | O | H | 0 | 237–239 | Free base |
| 2 | (+/−) | 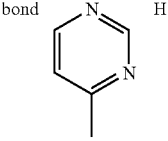 | bond | 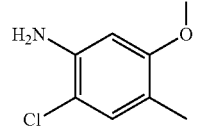 | H | H | H | H | O | H | 0 | 223–225 | Free base |
| 3 | (+/−) | 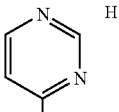 | bond | 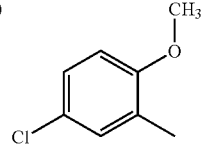 | H | H | H | H | O | H | 0 | 275–277 | Free base |
| 4 | (+/−) | 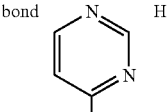 | bond | 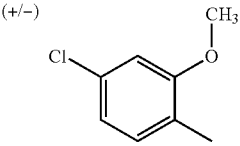 | H | H | H | H | O | H | 0 | 236–238 | Free base |
| 5 | (+/−) | 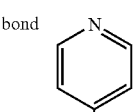 | bond | 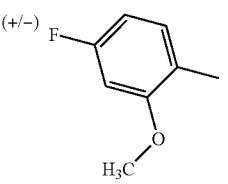 | H | H | H | H | O | H | 0 | 242–244 | Free base |
| 6 | (+/−) | 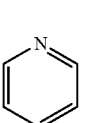 | bond | | H | H | H | H | O | H | 0 | 226–228 | Free base |

A list of chemical structures and physical data for compounds of the aforementioned formula (I), illustrating the present invention, is given in table 3. The compounds have been prepared according to the methods of the examples. In the table 3, m represents 1 and o represents 2, (Rot.) indicates the levorotatory or dextrorotatory properties of the enantiomeric compound.

TABLE 3
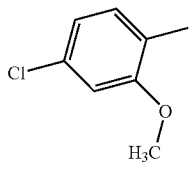
(I)
| No. | Rot | R2 | Z | R1 | R4 | R5 | R6 | R7 | Y | R3 | n | Mp ° C. | salt |
|---|---|---|---|---|---|---|---|---|---|---|---|---|---|
| 1 | (+/−) | 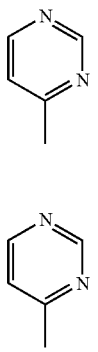 | bond | 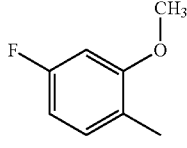 | H | H | H | H | O | H | 0 | 280-282 | Free base |
| 2 | (+/−) | 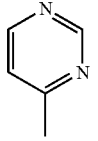 | bond | 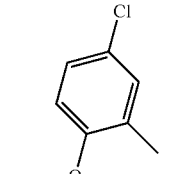 | H | H | H | H | O | H | 0 | 324-326 | Free base |
| 3 | (+/−) | 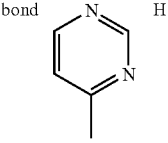 | bond | 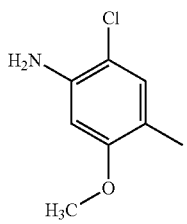 | H | H | H | H | O | H | 0 | 218-220 | Free base |
| 4 | (+/−) | 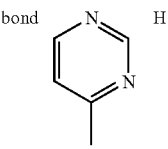 | bond | 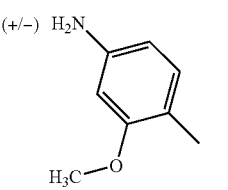 | H | H | H | H | O | H | 0 | 266-268 | Free base |
| 5 | (+/−) | 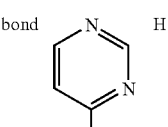 | bond | 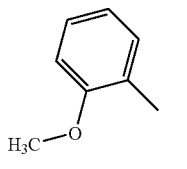 | H | H | H | H | O | H | 0 | 268-270 | Free base |
| 6 | (+/−) | 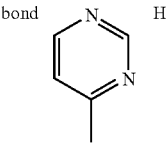 | bond | | H | H | H | H | O | H | 0 | 240-242 | Free base |

TABLE 3-continued
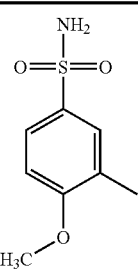
(I)
| No. | Rot | R2 | Z | R1 | R4 | R5 | R6 | R7 | Y | R3 | n | Mp °C. | salt |
|---|---|---|---|---|---|---|---|---|---|---|---|---|---|
| 7 | (+/−) | 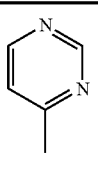 | bond | 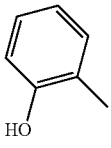 | H | H | H | H | O | H | 0 | 274-276 | Free base |
| 8 | (+/−) | 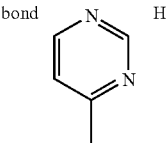 | bond | 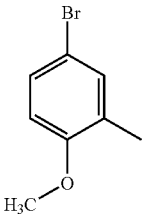 | H | H | H | H | O | H | 0 | 226-228 | Free base |
| 9 | (+/−) | 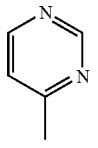 | bond | 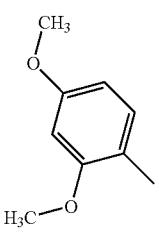 | H | H | H | H | O | H | 0 | 237-239 | Free base |
| 10 | (+/−) | 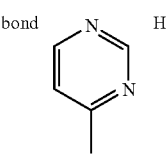 | bond | 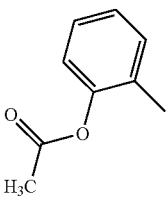 | H | H | H | H | O | H | 0 | 229-231 | Free base |
| 11 | (+/−) | 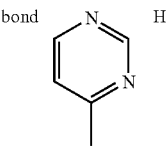 | bond | 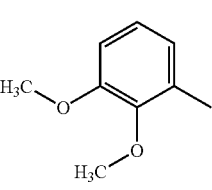 | H | H | H | H | O | H | 0 | 177-179 | Free base |
| 12 | (+/−) | 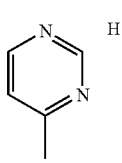 | bond | | H | H | H | H | O | H | 0 | 217-219 | Free base |

TABLE 3-continued
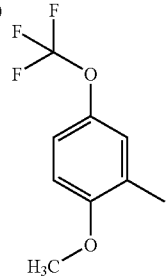
(I)
| No. | Rot | R2 | Z | R1 | R4 | R5 | R6 | R7 | Y | R3 | n | Mp °C. | salt |
|---|---|---|---|---|---|---|---|---|---|---|---|---|---|
| 13 | (+/−) | 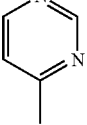 | bond | 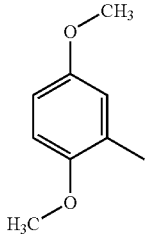 | H | H | H | H | O | H | 0 | 157-159 | Free base |
| 14 | (+/−) | 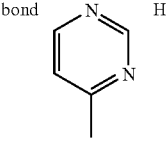 | bond | 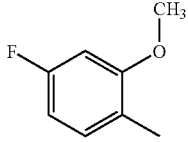 | H | H | H | H | O | H | 0 | 217-219 | Free base |
| 15 | (+) | 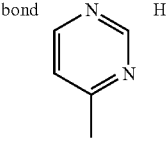 | bond | 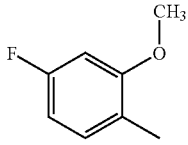 | H | H | H | H | O | H | 0 | 241-243 | Free base |
| 16 | (−) | 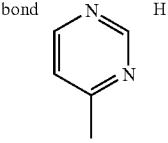 | bond | 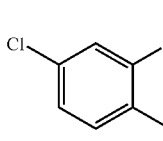 | H | H | H | H | O | H | 0 | 232-234 | Free base |
| 17 | (+/−) | 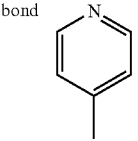 | bond | 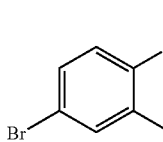 | H | H | H | H | O | H | 0 | 222-224 | Free base |
| 18 | (+/−) | 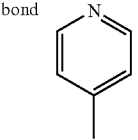 | bond | | H | H | H | H | O | H | 0 | 220-222 | Free base |

TABLE 3-continued
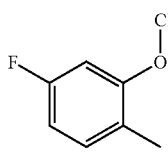
(I)
| No. | Rot | R2 | Z | R1 | R4 | R5 | R6 | R7 | Y | R3 | n | Mp ° C. | salt |
|---|---|---|---|---|---|---|---|---|---|---|---|---|---|
| 19 | (+/−) | 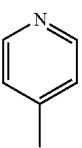 | bond | 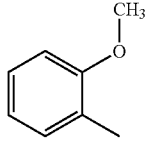 | H | H | H | H | O | H | 0 | 218-220 | Free base |
| 20 | (+/−) | 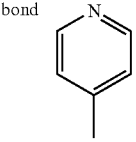 | bond | 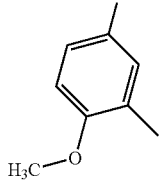 | H | H | H | H | O | H | 0 | 196-198 | Free base |
| 21 | (+/−) | 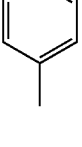 | bond | 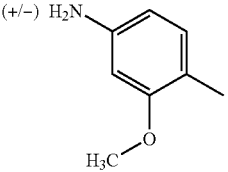 | H | H | H | H | O | H | 0 | 213-215 | Free base |
| 22 | (+/−) | 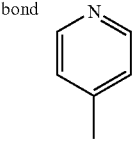 | bond | 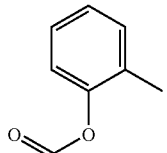 | H | H | H | H | O | H | 0 | 279-281 | Free base |
| 23 | (+/−) | 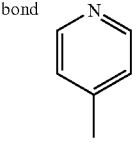 | bond | 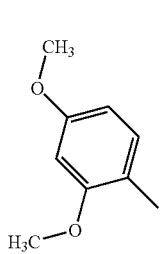 | H | H | H | H | O | H | 0 | 125-127 | Free base |
| 24 | (+/−) | 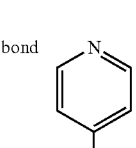 | bond | | H | H | H | H | O | H | 0 | 296-298 | Free base |

TABLE 3-continued

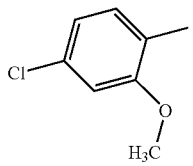

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 25 | (+) | 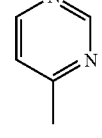 | bond | 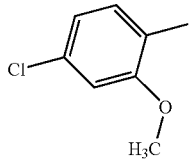 | H | H | H | H | O | H | 0 | 210-212 | Free base |
| 26 | (−) | 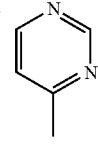 | bond | 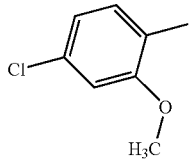 | H | H | H | H | O | H | 0 | 212-214 | Free base |

Test Example

Inhibitory Activity of the Medicament of the Present Invention against GSK3β

Two different protocols can be used.

In a first protocol: 7.5 µM of prephosphorylated GS1 peptide and 10 µM ATP (containing 300,000 cpm of 33P-ATP) were incubated in 25 mM Tris-HCl, pH 7.5, 0.6 mM DTT, 6 mM MgCl$_2$, 0.6 mM EGTA, 0.05 mg/ml BSA buffer for 1 hour at room temperature in the presence of GSK3beta (total reaction volume: 100 microliters).

In a second protocol: 4.1 µM of prephosphorylated GS1 peptide and 42 µM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta. Inhibitors were solubilized in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide used in the example was the same one as reported in Woodgett, J. R. (1989) Analytical Biochemistry 180, 237-241 and had the same sequence as reported therein, which reference is incorporated herein by reference in its entirety.

The GSK3β inhibitory activity of the compounds of the present invention are expressed in IC$_{50}$, and as an illustration the range of IC$_{50}$'s of the compounds in table 1 and table 2 are between 0.1 nanomolar to 3 micromolar concentrations. For example compound No. 33 of table 1 shows an IC$_{50}$ of 0.005 µM.

Formulation Example

1 Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

2 Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

1 Parenteral preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

Industrial Applicability

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:

1. A compound of formula (I) or a salt thereof:

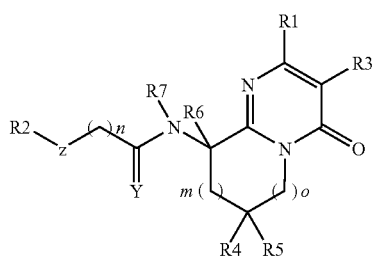

wherein:
Y represents two hydrogen atoms, a sulfur atom, an oxygen atom or a $C_{1-2}$ alkyl group and a hydrogen atom;
Z represents a bond, an oxygen atom, a nitrogen atom substituted by a hydrogen atom or a $C_{1-3}$ alkyl group, a sulfur atom, a methylene group optionally substituted by one or two groups chosen from a $C_{1-6}$ alkyl group, a hydroxyl group, a $C_{1-6}$ alkoxy group, a $C_{1-2}$ perhalogenated alkyl group or an amino group;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a benzene ring or a naphthalene ring; the rings being optionally substituted by 1 to 4 substituents selected from a $C_{1-6}$ alkyl group, $C_{3-7}$ cycloalkyl group, a $C_{3-7}$ cycloalkyl-$C_{1-6}$ alkyl group, a halogen atom, a $C_{1-2}$ perhalogenated alkyl group, a $C_{1-3}$ halogenated alkyl group, a hydroxyl group, a $C_{1-6}$ alkoxy group optionally substituted by a $C_{3-5}$ cycloalkyl group, a $C_{1-2}$ perhalogenated alkoxy group, a $C_{1-6}$ alkylsulfonyl group, a nitro, a cyano, an amino, a $C_{1-6}$ monoalkylamino group, a $C_{2-12}$ dialkylamino group, an acetoxy group or an aminosulfonyl group;
R3 represents a hydrogen atom, a $C_{1-6}$ alkyl group or a halogen atom;
R4 represents a hydrogen atom or a $C_{1-6}$ alkyl group;
R5 represents a hydrogen atom, a $C_{1-6}$ alkyl group optionally substituted by 1 to 4 substituents selected from a halogen atom, a phenyl group, a hydroxyl group or a $C_{1-6}$ alkoxy group;
R6 represents a hydrogen atom, a $C_{1-6}$ alkyl group or a halogen atom;
R7 represents a hydrogen atom or a $C_{1-6}$ alkyl group; and
n represents 0 to 3; m represents 0 to 1; o represents 0 to 2.

2. The compound or a salt thereof according to claim 1, wherein R1 represents an unsubstituted 4-pyridine ring or unsubstituted 4-pyrimidine ring.

3. The compound or a salt thereof according to claim 1, wherein:

R1 represents a 3- or 4-pyridine ring or alternatively a 4- or 5-pyrimidine ring; the rings being optionally substituted by a $C_{1-2}$ alkyl group, a $C_{1-2}$ alkoxy group or a halogen atom;
R2 represents a benzene ring or a naphthalene ring; the rings being optionally substituted by 1 to 4 substituents selected from a $C_{1-3}$ alkyl group, $C_{3-5}$ cycloalkyl group, a $C_{3-5}$ cycloalkyl-$C_{1-4}$ alkyl group, a halogen atom, a $C_{1-3}$ halogenated alkyl group, a hydroxyl group, a $C_{1-3}$ alkoxy group optionally substituted by a $C_{3-5}$ cycloalkyl group, a $C_{1-2}$ perhalogenated alkoxy group, a $C_{1-6}$ alkylsulfonyl group, a nitro, a cyano, an amino, a $C_{1-3}$ monoalkylamino group or a $C_{2-6}$ dialkylamino group;
R3 represents a hydrogen atom, a $C_{1-3}$ alkyl group or a halogen atom;
R4 represents a hydrogen atom or a $C_{1-3}$ alkyl group;
R5 represents a hydrogen atom, a $C_{1-3}$ alkoxy carbonyl group or a $C_{1-3}$ alkyl group optionally substituted by 1 to 4 substituents selected from a halogen atom, a phenyl group, a hydroxyl group or a $C_{1-3}$ alkoxy group;
R6 represents a hydrogen atom, a $C_{1-3}$ alkyl group or a halogen atom;
R7 represents a hydrogen atom or a $C_{1-3}$ alkyl group;
Y represents two hydrogen atoms, an oxygen atom or a $C_{1-2}$ alkyl group and a hydrogen atom;
Z represents a bond, an oxygen atom, a nitrogen atom substituted by a hydrogen atom or a $C_{1-3}$ alkyl group, a methylene group optionally substituted by one or two groups chosen from a $C_{1-3}$ alkyl group, a hydroxyl group, a $C_{1-3}$ alkoxy group, a $C_{1-2}$ perhalogenated alkyl group or an amino group;
n represents 0 to 3; m represents 0 or 1 and o represents 1 to 2.

4. The compound or a salt thereof according to claim 1, wherein:

R1 represents an unsubstituted 4-pyridine ring or 4-pyrimidine ring;
R2 represents a benzene ring or a naphthalene ring; the rings being optionally substituted by 1 to 4 substituents selected from a $C_{1-3}$ alkyl group, a $C_{1-2}$ perhalogenated alkyl group, a $C_{3-4}$ cycloalkyl group, a $C_{3-4}$ cycloalkyl-$C_{1-3}$ alkyl group, a halogen atom, a hydroxyl group, a nitro, a cyano, an amino, a $C_{1-3}$ alkoxy group optionally substituted by a $C_{3-4}$ cycloalkyl group, a $C_{1-2}$ perhalogenated alkoxy group or a $C_{1-3}$ alkylsulfonyl group;
R3 represents a hydrogen atom or a halogen atom;
R4 represents a hydrogen atom;
R5 represents a hydrogen atom;
R6 represents a hydrogen atom or a $C_{1-6}$ alkyl group;
R7 represents a hydrogen atom;
Y represents two hydrogen atoms, or an oxygen atom;
Z represents a bond, an oxygen atom, a nitrogen atom substituted by a hydrogen atom;
n represents 0 to 1;
m represents 0 to 1 and o represents 1 to 2.

5. The compound or a salt thereof according to claim 1 which is selected from the group consisting of:
(+/−) N-(4-Oxo-2-pyrimidin-4-yl-6,7,8,9-tetrahydro-4H-pyrido[1,2-a]pyrimidin-9-yl)benzamide;
(+/−) 2-Methoxy-N-(4-oxo-2-pyridin-4-yl-6,7,8,9-tetrahydro-4H-pyrido[1,2-a]pyrimidin-9-yl)benzamide;
(+/−) N-(4-Oxo-2-pyridin-4-yl-6,7,8,9-tetrahydro-4H-pyrido[1,2-a]pyrimidin-9-yl)-2-phenylacetamide;
(+/−) Phenyl(4-oxo-2-pyridin-4-yl-6,7,8,9-tetrahydro-4H-pyrido[1,2-a]pyrimidin-9-yl)carbamate;
(+/−) N-(4-Fluorophenyl)-N'-(4-oxo-2-pyrimidin-4-yl-6,7,8,9-tetrahydro-4H-pyrido[1,2-a]pyrimidin-9-yl)urea;

(+/−) N-(4-Oxo-2-pyridin-4-yl-6,7,8,9-tetrahydro-4H-pyrido[1,2-a]pyrimidin-9-yl)-N'-phenylurea;

(+/−) 9-[(2-Methoxybenzyl)amino]-2-pyridin-4-yl-6,7,8,9-tetrahydro-4H-pyrido[1,2-a]pyrimidin-4-one;

(+/−) 3-Fluoro-N-(4-oxo-2-pyrimidin-4-yl-6,7,8,9-tetrahydro-4H-pyrido[1,2-a]pyrimidin-9-yl)benzamide;

(+/−) 4-Isopropoxy-N-(4-oxo-2-pyridin-4-yl-6,7,8,9-tetrahydro-4H-pyrido[1,2-a]pyrimidin-9-yl)benzamide;

(+/−) 2-Chloro-N-(4-oxo-2-pyridin-4-yl-6,7,8,9-tetrahydro-4H-pyrido[1,2-a]pyrimidin-9-yl)benzamide;

(+/−) 4-Fluoro-N-(4-oxo-2-pyridin-4-yl-6,7,8,9-tetrahydro-4H-pyrido[1,2-a]pyrimidin-9-yl)benzamide;

(+/−) 3-Cyano-N-(4-oxo-2-pyridin-4-yl-6,7,8,9-tetrahydro-4H-pyrido[1,2-a]pyrimidin-9-yl)benzamide;

(+/−) 2-Chloro-5-fluoro-N-(4-oxo-2-pyridin-4-yl-6,7,8,9-tetrahydro-4H-pyrido[1,2-a]pyrimidin-9-yl)benzamide;

(+/−) 2-Methoxy-N-(4-oxo-2-pyrimidin-4-yl-6,7,8,9-tetrahydro-4H-pyrido[1,2-a]pyrimidin-9-yl)benzamide;

(+/−) 4-Fluoro-N-(4-oxo-2-pyridin-4-yl-6,7,8,9-tetrahydro-4H-pyrido[1,2-a]pyrimidin-9-yl)-2-(trifluoromethyl)benzamide;

(+/−) 4-Methoxy-N-(4-oxo-2-pyridin-4-yl-6,7,8,9-tetrahydro-4H-pyrido[1,2-a]pyrimidin-9-yl)-3-(trifluoromethyl)benzamide;

(+/−) N-(4-Oxo-2-pyridin-4-yl-6,7,8,9-tetrahydro-4H-pyrido[1,2-a]pyrimidin-9-yl)-2-(trifluoromethyl)benzamide;

(+/−) 2-Chloro-4-fluoro-5-nitro-N-(4-oxo-2-pyridin-4-yl-6,7,8,9-tetrahydro-4H-pyrido[1,2-a]pyrimidin-9-yl)benzamide;

(+/−) N-(4-Oxo-2-pyridin-4-yl-6,7,8,9-tetrahydro-4H-pyrido[1,2-a]pyrimidin-9-yl)-2-naphthamide;

(+/−) 3-Chloro-N-(4-oxo-2-pyridin-4-yl-6,7,8,9-tetrahydro-4H-pyrido[1,2-a]pyrimidin-9-yl)benzamide;

(+/−) 2,6-Dimethoxy-N-(4-oxo-2-pyrimidin-4-yl-6,7,8,9-tetrahydro-4H-pyrido[1,2-a]pyrimidin-9-yl)benzamide;

(+/−) 3-Methoxy-N-(4-oxo-2-pyrimidin-4-yl-6,7,8,9-tetrahydro-4H-pyrido[1,2-a]pyrimidin-9-yl)benzamide;

(+/−) 2-Fluoro-6-methoxy-N-(4-oxo-2-pyrimidin-4-yl-6,7,8,9-tetrahydro-4H-pyrido[1,2-a]pyrimidin-9-yl)benzamide;

(+/−) 4-Fluoro-2-methoxy-N-(4-oxo-2-pyridin-4-yl-6,7,8,9-tetrahydro-4H-pyrido[1,2-a]pyrimidin-9-yl)benzamide;

(+/−) 4-Chloro-2-methoxy-N-(4-oxo-2-pyrimidin-4-yl-6,7,8,9-tetrahydro-4H-pyrido[1,2-a]pyrimidin-9-yl)benzamide;

(+/−) 2-Ethoxy-N-(4-oxo-2-pyridin-4-yl-6,7,8,9-tetrahydro-4H-pyrido[1,2-a]pyrimidin-9-yl)benzamide;

(+/−) N-(3-Bromo-4-oxo-2-pyridin-4-yl-6,7,8,9-tetrahydro-4H-pyrido[1,2-a]pyrimidin-9-yl)-2-methoxybenzamide;

(+/−) 4-Amino-5-chloro-2-methoxy-N-(4-oxo-2-pyridin-4-yl-6,7,8,9-tetrahydro-4H-pyrido[1,2-a]pyrimidin-9-yl)benzamide;

(+/−) N-(4-Oxo-2-pyridin-4-yl-6,7,8,9-tetrahydro-4H-pyrido[1,2-a]pyrimidin-9-yl)-2-(trifluoromethoxy)benzamide;

(+/−) 2-Isopropoxy-N-(4-oxo-2-pyridin-4-yl-6,7,8,9-tetrahydro-4H-pyrido[1,2-a]pyrimidin-9-yl)benzamide;

(+/−) 2-(Cyclopropylmethoxy)-N-(4-oxo-2-pyridin-4-yl-6,7,8,9-tetrahydro-4H-pyrido[1,2-a]pyrimidin-9-yl)benzamide;

(+/−) 4-Amino-5-chloro-2-methoxy-N-(4-oxo-2-pyrimidin-4-yl-6,7,8,9-tetrahydro-4H-pyrido[1,2-a]pyrimidin-9-yl)benzamide;

(+/−) 4-Fluoro-2-methoxy-N-(4-oxo-2-pyrimidin-4-yl-6,7,8,9-tetrahydro-4H-pyrido[1,2-a]pyrimidin-9-yl)benzamide;

(+/−) 2-(Cyclopropylmethoxy)-N-(4-oxo-2-pyrimidin-4-yl-6,7,8,9-tetrahydro-4H-pyrido[1,2-a]pyrimidin-9-yl)benzamide;

(+/−) N-(4-Oxo-2-pyrimidin-4-yl-6,7,8,9-tetrahydro-4H-pyrido[1,2-a]pyrimidin-9-yl)-2-naphthamide;

(+/−) 3-Chloro-N-(4-oxo-2-pyrimidin-4-yl-6,7,8,9-tetrahydro-4H-pyrido[1,2-a]pyrimidin-9-yl)benzamide;

(+/−) 5-Chloro-2-methoxy-N-(4-oxo-2-pyrimidin-4-yl-6,7,8,9-tetrahydro-4H-pyrido[1,2-a]pyrimidin-9-yl)benzamide;

(+/−) 4-Amino-2-methoxy-N-(4-oxo-2-pyrimidin-4-yl-6,7,8,9-tetrahydro-4H-pyrido[1,2-a]pyrimidin-9-yl)benzamide;

(+/−) 2-Methoxy-N-(4-oxo-2-pyrimidin-4-yl-6,7,8,9-tetrahydro-4H-pyrido[1,2-a]pyrimidin-9-yl)-4-trifluoromethyl-benzamide;

(+/−) 5-(Ethylsulfonyl)-2-methoxy-N-(4-oxo-2-pyrimidin-4-yl-6,7,8,9-tetrahydro-4H-pyrido[1,2-a]pyrimidin-9-yl)benzamide;

(+/−) 2,3-Dimethoxy-N-(4-oxo-2-pyrimidin-4-yl-6,7,8,9-tetrahydro-4H-pyrido[1,2-a]pyrimidin-9-yl)benzamide;

(−) 4-Chloro-2-methoxy-N-(4-oxo-2-pyrimidin-4-yl-6,7,8,9-tetrahydro-4H-pyrido[1,2-a]pyrimidin-9-yl)benzamide;

(+) 4-Chloro-2-methoxy-N-(4-oxo-2-pyrimidin-4-yl-6,7,8,9-tetrahydro-4H-pyrido[1,2-a]pyrimidin-9-yl)benzamide;

(+/−) 5-Bromo-2-methoxy-N-(4-oxo-2-pyrimidin-4-yl-6,7,8,9-tetrahydro-4H-pyrido[1,2-a]pyrimidin-9-yl)benzamide;

(+/−) 2-{[(4-Oxo-2-pyrimidin-4-yl-6,7,8,9-tetrahydro-4H-pyrido[1,2-a]pyrimidin-9-yl)amino]carbonyl}phenyl acetate;

(+/−) 2-Hydroxy-N-(4-oxo-2-pyrimidin-4-yl-6,7,8,9-tetrahydro-4H-pyrido[1,2-a]pyrimidin-9-yl)benzamide;

(+/−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide;

(+) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide;

(−) 4-Chloro-2-methoxy-N-(9-methyl-4-oxo-2-pyrimidin-4-yl-6,7,8,9-tetrahydro-4H-pyrido[1,2-a]pyrimidin-9-yl)benzamide;

(+/−) 4-Chloro-2-methoxy-N-methyl-N-(4-oxo-2-pyrimidin-4-yl-6,7,8,9-tetrahydro-4H-pyrido[1,2-a]pyrimidin-9-yl)benzamide;

(+) 4-Fluoro-2-methoxy-N-(4-oxo-2-pyrimidin-4-yl-6,7,8,9-tetrahydro-4H-pyrido[1,2-a]pyrimidin-9-yl)benzamide;

(−) 4-Fluoro-2-methoxy-N-(4-oxo-2-pyrimidin-4-yl-6,7,8,9-tetrahydro-4H-pyrido[1,2-a]pyrimidin-9-yl)benzamide;

(+/−) 5-Chloro-2-methoxy-N-(9-methyl-4-oxo-2-pyrimidin-4-yl-6,7,8,9-tetrahydro-4H-pyrido[1,2-a]pyrimidin-9-yl)-benzamide;

(+/−) 4-Fluoro-2-methoxy-N-(9-methyl-4-oxo-2-pyrimidin-4-yl-6,7,8,9-tetrahydro-4H-pyrido[1,2-a]pyrimidin-9-yl)-benzamide;

(+/−) 4-Amino-5-chloro-2-methoxy-N-(9-methyl-4-oxo-2-pyrimidin-4-yl-6,7,8,9-tetrahydro-4H-pyrido[1,2-a]pyrimidin-9-yl)-benzamide;
(+/−) 2-Methoxy-N-(9-methyl-4-oxo-2-pyrimidin-4-yl-6,7,8,9-tetrahydro-4H-pyrido[1,2-a]pyrimidin-9-yl)-4-trifluoromethyl-benzamide;
(+/−) 2-Fluoro-6-methoxy-N-(9-methyl-4-oxo-2-pyrimidin-4-yl-6,7,8,9-tetrahydro-4H-pyrido[1,2-a]pyrimidin-9-yl)-benzamide;
(+/−) 2-Methoxy-N-(9-methyl-4-oxo-2-pyrimidin-4-yl-6,7,8,9-tetrahydro-4H-pyrido[1,2-a]pyrimidin-9-yl)-benzamide;
(+/−) 5-Bromo-2-methoxy-N-(9-methyl-4-oxo-2-pyrimidin-4-yl-6,7,8,9-tetrahydro-4H-pyrido[1,2-a]pyrimidin-9-yl)-benzamide;
(+/−)-4-Dimethylamino-2-methoxy-N-(9-methyl-4-oxo-2-pyrimidin-4-yl-6,7,8,9-tetrahydro-4H-pyrido[1,2-a]pyrimidin-9-yl)-benzamide;
(+/−)-2,4-Dimethoxy-N-(9-methyl-4-oxo-2-pyrimidin-4-yl-6,7,8,9-tetrahydro-4H-pyrido[1,2-a]pyrimidin-9-yl)-benzamide;
(+/−) 4-Chloro-2-methoxy-N-(4-oxo-2-pyrimidin-4-yl-4,6,7,8-tetrahydro-pyrrolo[1,2-a]pyrimidin-8-yl)-benzamide;
(+/−) 4-Fluoro-2-methoxy-N-(4-oxo-2-pyrimidin-4-yl-4,6,7,8-tetrahydro-pyrrolo[1,2-a]pyrimidin-8-yl)-benzamide;
(+/−) 4-Amino-5-chloro-2-methoxy-N-(4-oxo-2-pyrimidin-4-yl-4,6,7,8-tetrahydro-pyrrolo[1,2-a]pyrimidin-8-yl)-benzamide;
(+/−) 5-Chloro-2-methoxy-N-(4-oxo-2-pyrimidin-4-yl-4,6,7,8-tetrahydro-pyrrolo[1,2-a]pyrimidin-8-yl)-benzamide;
(+/−) 4-Chloro-2-methoxy-N-(4-oxo-2-pyridin-4-yl-4,6,7,8-tetrahydro-pyrrolo[1,2-a]pyrimidin-8-yl)-benzamide;
(+/−) 4-Fluoro-2-methoxy-N-(4-oxo-2-pyridin-4-yl-4,6,7,8-tetrahydro-pyrrolo[1,2-a]pyrimidin-8-y1)-benzamide;
(+/−) 4-Chloro-2-methoxy-N-(4-oxo-2-pyrimidin-4-yl-4,6,7,8,9,10-hexahydropyrimido[1,2-a]azepin-10-yl)benzamide;
(+/−) 4-Fluoro-2-methoxy-N-(4-oxo-2-pyrimidin-4-yl-4,6,7,8,9,10-hexahydropyrimido[1,2-a]azepin-10-yl)benzamide;
(+/−) 5-Chloro-2-methoxy-N-(4-oxo-2-pyrimidin-4-yl-4,6,7,8,9,10-hexahydropyrimido[1,2-a]azepin-10-yl)benzamide;
(+/−) 4-Amino-5-chloro-2-methoxy-N-(4-oxo-2-pyrimidin-4-yl-4,6,7,8,9,10-hexahydropyrimido[1,2-a]azepin-10-yl)benzamide;
(+/−) 4-Amino-2-methoxy-N-(4-oxo-2-pyrimidin-4-yl-4,6,7,8,9,10-hexahydropyrimido[1,2-a]azepin-10-yl)benzamide;
(+/−) 2-Methoxy-N-(4-oxo-2-pyrimidin-4-yl-4,6,7,8,9,10-hexahydropyrimido[1,2-a]azepin-10-yl)benzamide;
(+/−) 5-(Aminosulfonyl)-2-methoxy-N-(4-oxo-2-pyrimidin-4-yl-4,6,7,8,9,10-hexahydropyrimido[1,2-a]azepin-10-yl)benzamide;
(+/−) 2-Hydroxy-N-(4-oxo-2-pyrimidin-4-yl-4,6,7,8,9,10-hexahydropyrimido[1,2-a]azepin-10-yl)benzamide;
(+/−) 5-Bromo-2-methoxy-N-(4-oxo-2-pyrimidin-4-yl-4,6,7,8,9,10-hexahydropyrimido[1,2-a]azepin-10-yl)benzamide;
(+/−) 2,4-Dimethoxy-N-(4-oxo-2-pyrimidin-4-yl-4,6,7,8,9,10-hexahydropyrimido[1,2-a]azepin-10-yl)benzamide;
(+/−) 2-{[(4-Oxo-2-pyrimidin-4-yl-4,6,7,8,9,10-hexahydropyrimido[1,2-a]azepin-10-yl)amino]carbonyl}phenyl acetate;
(+/−) 2,3-Dimethoxy-N-(4-oxo-2-pyrimidin-4-yl-4,6,7,8,9,10-hexahydropyrimido[1,2-a]azepin-10-yl)benzamide;
(+/−) 2-Methoxy-N-(4-oxo-2-pyrimidin-4-yl-4,6,7,8,9,10-hexahydropyrimido[1,2-a]azepin-10-yl)-5-(trifluoromethoxy)benzamide;
(+/−) 2,5-Dimethoxy-N-(4-oxo-2-pyrimidin-4-yl-4,6,7,8,9,10-hexahydropyrimido[1,2-a]azepin-10-yl)benzamide;
(+) 4-Fluoro-2-methoxy-N-(4-oxo-2-pyrimidin-4-yl-4,6,7,8,9,10-hexahydropyrimido[1,2-a]azepin-10-yl)benzamide;
(−) 4-Fluoro-2-methoxy-N-(4-oxo-2-pyrimidin-4-yl-4,6,7,8,9,10-hexahydropyrimido[1,2-a]azepin-10-yl)benzamide;
(+/−) 4-Chloro-2-methoxy-N-(4-oxo-2-pyridin-4-yl-4,6,7,8,9,10-hexahydropyrimido[1,2-a]azepin-10-yl)benzamide;
(+/−) 5-Bromo-2-methoxy-N-(4-oxo-2-pyridin-4-yl-4,6,7,8,9,10-hexahydropyrimido[1,2-a]azepin-10-yl)benzamide;
(+/−) 4-Fluoro-2-methoxy-N-(4-oxo-2-pyridin-4-yl-4,6,7,8,9,10-hexahydropyrimido[1,2-a]azepin-10-yl)benzamide;
(+/−) 2-Methoxy-N-(4-oxo-2-pyridin-4-yl-4,6,7,8,9,10-hexahydropyrimido[1,2-a]azepin-10-yl)benzamide;
(+/−) 5-Chloro-2-methoxy-N-(4-oxo-2-pyridin-4-yl-4,6,7,8,9,10-hexahydropyrimido[1,2-a]azepin-10-yl)benzamide;
(+/−) 4-Amino-2-methoxy-N-(4-oxo-2-pyridin-4-yl-4,6,7,8,9,10-hexahydropyrimido[1,2-a]azepin-10-yl)benzamide;
(+/−) 2-{[(4-Oxo-2-pyridin-4-yl-4,6,7,8,9,10-hexahydropyrimido[1,2-a]azepin-10-yl)amino]carbonyl}phenyl acetate;
(+/−) 2,4-Dimethoxy-N-(4-oxo-2-pyridin-4-yl-4,6,7,8,9,10-hexahydropyrimido[1,2-a]azepin-10-yl)benzamide;
(+) 4-chloro-2-methoxy-N-(4-oxo-2-pyrimidin-4-yl-4,6,7,8,9,10-hexahydropyrimido[1,2-a]azepin-10-yl)benzamide; and
(−) 4-chloro-2-methoxy-N-(4-oxo-2-pyrimidin-4-yl-4,6,7,8,9,10-hexahydropyrimido[1,2-a]azepin-10-yl)benzamide.

6. A pharmaceutical composition comprising a compound of formula (I) or a pharmaceutically acceptable salt thereof according to claim 1 in combination with at least one pharmaceutically acceptable excipient.

7. A pharmaceutical composition comprising a compound of formula (I) or a pharmaceutically acceptable salt thereof according to claim 2 in combination with at least one pharmaceutically acceptable excipient.

8. A pharmaceutical composition comprising a compound of formula (I) or a pharmaceutically acceptable salt thereof according to claim 3 in combination with at least one pharmaceutically acceptable excipient.

9. A pharmaceutical composition comprising a compound of formula (I) or a pharmaceutically acceptable salt thereof according to claim 4 in combination with at least one pharmaceutically acceptable excipient.

10. A pharmaceutical composition comprising a compound of formula (I) or a pharmaceutically acceptable salt thereof according to claim 5 in combination with at least one pharmaceutically acceptable excipient.

* * * * *